(12) United States Patent
Guzi et al.

(10) Patent No.: US 6,969,718 B2
(45) Date of Patent: Nov. 29, 2005

(54) 17-β HYDROXYSTEROID DEHYDROGENASE TYPE 3 INHIBITORS FOR THE TREATMENT OF ANDROGEN DEPENDENT DISEASES

(75) Inventors: Timothy J. Guzi, Chatham, NJ (US); Kamil Paruch, Cranford, NJ (US)

(73) Assignee: Schering Corporation, Kenilworth, NJ (US)

( * ) Notice: Subject to any disclaimer, the term of this patent is extended or adjusted under 35 U.S.C. 154(b) by 123 days.

(21) Appl. No.: 10/271,358

(22) Filed: Oct. 15, 2002

(65) Prior Publication Data

US 2003/0232837 A1 Dec. 18, 2003

Related U.S. Application Data

(60) Provisional application No. 60/330,066, filed on Oct. 17, 2001.

(51) Int. Cl.[7] .................... A61K 31/497; C07D 401/00
(52) U.S. Cl. .................... 514/253.01; 544/360
(58) Field of Search ............... 514/253.01, 253.02; 544/360

(56) References Cited

U.S. PATENT DOCUMENTS

| | | | |
|---|---|---|---|
| 5,350,852 A | 9/1994 | Emonds-Alt et al. | 544/336 |
| 5,432,175 A | 7/1995 | Piwinski et al. | 514/252 |
| 5,620,989 A | 4/1997 | Harrison et al. | 514/317 |
| 5,654,316 A | 8/1997 | Carruthers et al. | 514/307 |
| 5,665,735 A | 9/1997 | Friary et al. | 514/318 |
| 5,688,960 A | 11/1997 | Shankar | 546/202 |
| 5,691,362 A | 11/1997 | McCormick et al. | 514/339 |
| 5,696,267 A | 12/1997 | Reichard et al. | 546/217 |
| 5,719,156 A | 2/1998 | Shue et al. | 514/255 |
| 5,760,018 A | 6/1998 | Baker et al. | 514/63 |
| 5,783,579 A | 7/1998 | McCormick | 514/255 |
| 5,789,422 A | 8/1998 | Reichard et al. | 514/327 |
| 5,795,894 A | 8/1998 | Shue et al. | 514/253 |
| 5,840,725 A | 11/1998 | Reichard et al. | 514/252 |
| 5,892,039 A | 4/1999 | Shue et al. | 544/360 |
| 5,945,428 A | 8/1999 | Shih et al. | 514/278 |
| 5,968,929 A | 10/1999 | Blythin et al. | 514/215 |
| 6,063,926 A | 5/2000 | Reichard et al. | 546/187 |
| 6,204,265 B1 | 3/2001 | Reichard et al. | 514/235.8 |

FOREIGN PATENT DOCUMENTS

| | | |
|---|---|---|
| DE | 1930818 | 1/1970 |
| DE | 2304153 | 8/1974 |
| EP | 0655442 A1 | 5/1995 |
| FR | 2215235 | 8/1974 |
| WO | WO86/01105 | 2/1986 |
| WO | WO90/10462 | 9/1990 |
| WO | WO91/00731 | 1/1991 |
| WO | WO91/00733 | 1/1991 |
| WO | WO 92/06971 | 4/1992 |
| WO | WO 93/20063 | 10/1993 |
| WO | WO94/10165 | 5/1994 |
| WO | WO94/13639 | 6/1994 |
| WO | WO94/26767 | 11/1994 |
| WO | WO94/29309 | 12/1994 |
| WO | WO95/19344 | 7/1995 |
| WO | WO96/26201 | 8/1996 |
| WO | WO 96/31501 | 10/1996 |
| WO | WO97/11162 | 3/1997 |
| WO | WO 00/39119 | * 7/2000 |
| WO | WO00/43008 | 7/2000 |

OTHER PUBLICATIONS

Al–Dabbagh and Smith, "Species differences in oxidative drug metabolism: some basic considerations." Archives of toxicology. Supplement. Archiv fur Toxikologie. supplement, vol. 7, pp. 219–231 (1984).*

Hans Bundgaard, Design of Prodrugs, p. 1. © 1985 Elsevier Science Publishers.*

Richard B. Silverman, The Organic Chemistry of Drug Design and Drug Action, pp. 352–400. © 1992 Academic Press, Inc.*

Hawley's Condensed Chemical Dictionary, 12th ed., Richard J. Lewis, Sr. , © 1993 by Van Nostrand Reinhold. p. 594.*

Concise Chemical Dictionary, edited by Drs. Hans–Dieter Jakubke and Hans Jeschkeit, © 1993 by Walter de Gruyter & Co., p. 490.*

(Continued)

*Primary Examiner*—James O. Wilson
*Assistant Examiner*—Zachary C. Tucker
(74) *Attorney, Agent, or Firm*—Palaiyur S. Kalyanaraman; Allan N. Kutzenco; Margaret M. Albanese

(57) ABSTRACT

There are disclosed compounds of the formula (I):

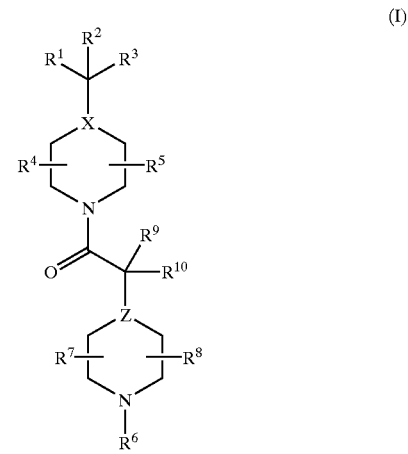

prodrugs thereof, or pharmaceutically acceptable salts of the compounds or of said prodrugs which are useful as inhibitors of Type 3 17β-Hydroxysteroid Dehydrogenase. Also disclosed are pharmaceutical compositions containing said compounds and their use for the treatment or prevention of androgen dependent diseases.

18 Claims, No Drawings

OTHER PUBLICATIONS

McGraw–Hill Dictionary of Chemical Terms, 3rd ed. edited by Sybil P. Parker, © 1984 McGraw–Hill, Inc., p. 200.*

Poirier, Donald, "Inhibitors of 17–beta–Hydroxysteroid Dehydrogenases" Current Medicinal Chemistry, vol. 10, pp. 453–477 (2003).*

Goodman & Gilman's The Pharmacological Basis of Therapeutics, 10th ed., pp. 1635–1648, McGraw–Hill Medical Publishing Division © 2001.*

The Merck Manual, 16th ed., pp. 1092–1093, 2277–2278 and 2429–2431, Merck Research Laboratories, Merck & Co., Rahway, NJ © 1992.*

Smith et al, "Inhibitors of steroidogenesis as agents for the treatment of hormone–dependent cancers" Expert Opinion on Therapeutic Patents, vol. 11(5), pp. 789–824 (2001).*

Debeljuk, L., Lasaga, M., *Modulation of the hypothalamo–pituitary–gonadal axis and the pineal gland by neurokinin A, neuropeptide K and neuropeptide γ*, Peptides 20 (1999), 285–299.

* cited by examiner

17-β HYDROXYSTEROID DEHYDROGENASE TYPE 3 INHIBITORS FOR THE TREATMENT OF ANDROGEN DEPENDENT DISEASES

CROSS-REFERENCE TO RELATED APPLICATION

This application claims priority to U.S. Provisional Application No. 60/330,066, filed Oct. 17, 2001.

BACKGROUND

1. Field of the Invention

The invention relates to novel inhibitors of Type 3 17β-Hydroxysteroid Dehydrogenase, pharmaceutical compositions containing the compounds and the use of the compounds for the treatment or prevention of androgen dependent diseases.

2. Description of Related Art

Androgen dependent diseases, for example, diseases whose onset or progress is aided by androgenic activity, are well known. These diseases include but are not limited to prostate cancer, benign prostatic hyperplasia, acne, seborrhea, hirsutism, androgenic alopecia, precocious puberty, adrenal hyperplasia and polycystic ovarian syndrome. Estrogen dependent diseases, i.e. diseases whose onset or progress is aided by estrogenic activity are also well known. These include but are not limited to breast cancer, endometriosis, leiomyoma and precocious puberty.

Androgenic and estrogenic activity may be suppressed by administering androgen receptor antagonists or estrogen receptor antagonists respectively. See e.g. WO 94/26767 and WO 96/26201. Androgenic and estrogenic activity may also be reduced by suppressing androgen or estrogen biosynthesis using inhibitors of enzymes that catalyze one or more steps of such biosynthesis. Type 3 17β-Hydroxysteroid Dehydrogenase (17β-HSD3) is the primary enzyme that converts androstenedione to testosterone in the testes. Androgenic and estrogenic activity may also be reduced by suppressing ovarian or testicular secretions by known methods. See e.g. WO 90/10462, WO 91/00731, WO 91/00733, and WO 86/01105. Type 5 17B-Hydroxysteriod Dehydrogenase is described in WO 97/11162. Novel inhibitors of both Type 3 and Type 5 17B-Hyroxysteroid Dehydrogenase are described in WO 99/46279.

U.S. Pat. No. 5,665,735 discloses compounds useful in the treatment of asthma, allergy and inflammation, which are of the formula:

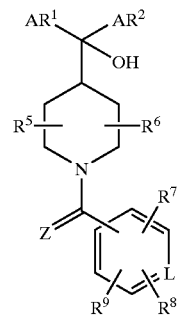

or a pharmaceutically acceptable salt or solvate thereof, wherein:

$AR^1$ (or $Ar^1$) represents

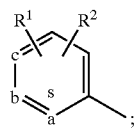

$AR^2$ (or $Ar^2$) represents

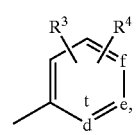

or a five-membered heterocyclic aromatic group selected from the group consisting of Formulas I to XII:

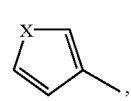
(I)

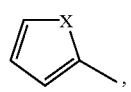
(II)

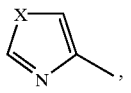
(III)

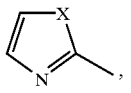
(IV)

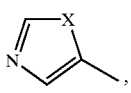
(V)

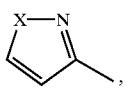
(VI)

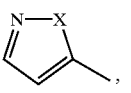
(VII)

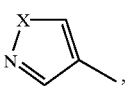
(VIII)

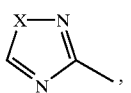
(IX)

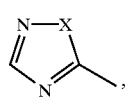
(X)

3
-continued

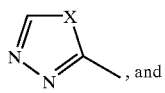, and (XI)

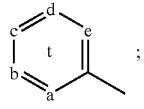 (XII)

wherein X represents O, S.

U.S. Pat. No. 5,432,175 discloses compounds which possess anti-allergic and anti-inflammatory activity and are of the formula:

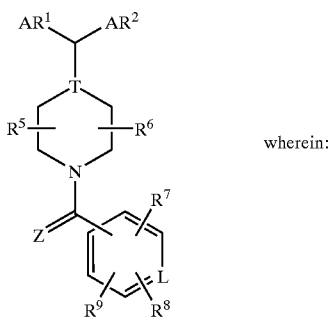

wherein:

$AR^1$ represents 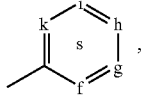;

$AR^2$ represents 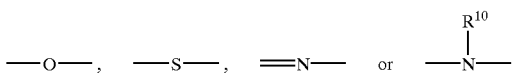, or a five-membered heterocyclic aromatic group containing at least one —O—, —S—, =N— or —N(R$^{10}$)— in the ring structure,

T represents CH, C or N,

Current therapies for the treatment of androgenic and estrogenic dependent diseases include the use of glucocorticoids to block adrenal secretions, and luteinizing hormone releasing hormone (LHRH) agonists which cause medical castration. Both therapies are associated with undesirable side effects. An improved therapy would include compounds that specifically inhibit type 3 17β-Hydroxysteroid dehydrogenase, while avoiding inhibition of other 17β-Hydroxysteroid dehydrogenases. Such an improvement is provided by this invention.

4
SUMMARY OF THE INVENTION

The present invention provides novel compounds represented by Formula (I):

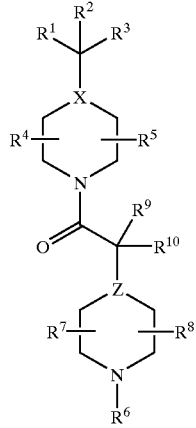 (I)

a prodrug thereof, or a pharmaceutically acceptable salt or solvate of the compound or of the prodrug wherein, $R^1$ is selected from the group consisting of aryl, heteroaryl, arylalkyl, heteroarylalkyl and diphenylalkyl, each optionally substituted with one to six groups selected from the group consisting of:
a) halogen;
b) —OCF$_3$ or —OCHF$_2$;
c) —CF$_3$;
d) —CN;
e) alkyl or R$^{18}$-alkyl;
f) heteroalkyl or R$^{18}$-heteroalkyl;
g) aryl or R$^{18}$-aryl;
h) heteroaryl or R$^{18}$-heteroaryl;
i) arylalkyl or R$^{18}$-arylalkyl;
j) heteroarylalkyl or R$^{18}$-heteroarylalkyl;
k) hydroxy;
l) alkoxy;
m) aryloxy;
n) —SO$_2$-alkyl;
o) —NR$^{11}$R$^{12}$;
p) —N(R$^{11}$)C(O)R$^{13}$,
q) methylenedioxy;
r) difluoromethylenedioxy;
s) trifluoroalkoxy;
t) —SCH$_3$ or —SCF$_3$; and
u) —SO$_2$CF$_3$ or —NHSO$_2$CF$_3$;

$R^2$ and $R^3$ are each independently selected from the group consisting of: H, —OH, alkoxy, alkyl, cycloalkyl, heterocycloalkyl, cycloalkylalkyl, trifluoroalkyl, heteroalkyl, arylalkyl, heteroarylalkyl, arylalkoxy, heteroarylalkoxy, —(CH$_2$)$_n$—NR$^{11}$R$^{12}$ and —(CH$_2$)$_n$—SR$^{11}$, provided that when X is N, then $R^2$ and $R^3$ are each not —OH, alkoxy, arylalkoxy or heteroarylalkoxy;

$R^4$, $R^5$, $R^7$ and $R^8$ are each independently selected from the group consisting of: H, —OR$^{14}$, —NR$^{11}$R$^{12}$, —N(R$^{11}$)C(O)R$^{13}$, alkyl, aryl, cycloalkyl, arylalkyl, heteroalkyl, heteroaryl, heteroarylalkyl, heterocycloalkyl,

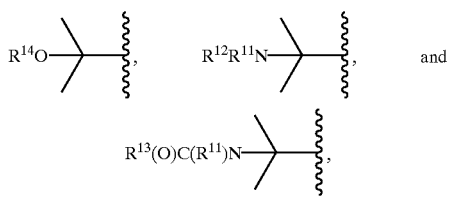

provided that when Z and/or X is N, then $R^4$, $R^5$, $R^7$ and $R^8$ are each not —$OR^{14}$, —$NR^{11}R^{12}$ or —$N(R^{11})C(O)R^{13}$;

$R^6$ is selected from the group consisting of —$C(O)R^{15}$ and —$SO_2R^{15}$;

$R^9$ and $R^{10}$ are each independently selected from the group consisting of: H, F, —$CF_3$, —$CHF_2$, alkyl, cycloalkyl, arylalkyl, heteroalkyl, heteroarylalkyl, heterocycloalkyl, hydroxy, alkoxy, aryloxy, —$NR^{11}R^{12}$ and —$N(R^{11})C(O)R^{13}$, provided that when Z is N, then $R^9$ and $R^{10}$ are each not F, hydroxy, alkoxy, aryloxy, —$NR^{11}R^{12}$ or —$N(R^{11})C(O)R^{13}$;

$R^{11}$ is selected from the group consisting of H, alkyl, aryl and heteroaryl;

$R^{12}$ is selected from the group consisting of H, alkyl, aryl and heteroaryl;

$R^{13}$ is selected from the group consisting of alkyl, alkoxy and aryloxy;

$R^{14}$ is selected from the group consisting of H, alkyl, aryl and heteroaryl;

$R^{15}$ is selected from the group consisting of: —$NR^{16}R^{17}$, —$OR^{16}$, alkyl, cycloalkyl, heterocycloalkyl, aryl, arylalkyl and heteroarylalkyl, each optionally substituted with $R^{18}$;

$R^{16}$ and $R^{17}$ are each independently selected from the group consisting of: alkyl, aryl, arylalkyl, heteroalkyl and heteroaryl, each optionally substituted with $R^{18}$, and H, provided that when $R^{15}$ is —$OR^{16}$, then $R^{16}$ is not H;

$R^{18}$ is one to four substituents each independently selected from the group consisting of: lower alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl;

X and Z are each independently selected from the group consisting of C and N; and n is 1–4.

Compounds represented by formula (I) are useful for the treatment or prevention of androgen dependent diseases, including, but not limited to, prostate cancer, benign prostatic hyperplasia and prostatic intraepithelial neoplasia. Another aspect of the invention comprises a pharmaceutical composition comprising a compound of formula (I), alone or with another active agent, and a pharmaceutically acceptable carrier or excipient therefore. The inventive compounds and compositions can be used alone or in combination with other active agents and/or methods of treatment for treating androgen dependent diseases.

A further understanding of the invention will be had from the following detailed description and claims.

DETAILED DESCRIPTION OF THE PREFERRED EMBODIMENTS

Unless where indicated otherwise, the following definitions apply throughout the present specification and claims.

These definitions apply regardless of whether a term is used by itself or in combination with other terms. Hence the definition of "alkyl" applies to "alkyl" as well as to the "alkyl" portions of "alkoxy", etc.

Unless otherwise known, stated or shown to be to the contrary, the point of attachment for a multiple term substituent (multiple terms that are combined to identify a single moiety) to a subject structure is through the last named term of the multiple term. For example, a cycloalkylalkyl substituent attaches to a targeted through the latter "alkyl" portion of the substituent (e.g., Structure-alkyl-cycloalkyl).

When any variable occurs more than one time in any constituent (e.g., $R_2$), its definition on each occurrence is independent of its definition at every other occurrence. Also, combinations of substituents and/or variables are permissible only if such combinations result in stable compounds.

Unless stated, shown or otherwise known to be the contrary, all atoms illustrated in chemical formulas for covalent compounds possess normal valencies. Thus, hydrogen atoms, double bonds, triple bonds and ring structures need not be expressly depicted in a general chemical formula.

Double bonds, where appropriate, may be represented by the presence of parentheses around an atom in a chemical formula. For example, a carbonyl functionality, —CO—, may also be represented in a chemical formula by —C(O)— or —C(=O)—. Similarly, a double bond between a sulfur atom and an oxygen atom may be represented in a chemical formula by —SO—, —S(O)— or —S(=O)—. One skilled in the art will be able to determine the presence or absence of double (and triple bonds) in a covalently-bonded molecule. For instance, it is readily recognized that a carboxyl functionality may be represented by —COOH, —C(O)OH, —C(=O)OH or —$CO_2H$.

The term "substituted," as used herein, means the replacement of one or more atoms or radicals, usually hydrogen atoms, in a given structure with an atom or radical selected from a specified group. In the situations where more than one atom or radical may be replaced with a substituent selected from the same specified group, the substituents may be, unless otherwise specified, either the same or different at every position. Radicals of specified groups, such as alkyl, cycloalkyl, heterocycloalkyl, aryl and heteroaryl groups, independently of or together with one another, may be substituents on any of the specified groups, unless otherwise indicated.

"Alkyl" represents a straight or branched saturated hydrocarbon chain having the designated number of carbon atoms. Preferably the number of carbon atoms is 1 to 20, more preferably 1 to 10, most preferably the number of carbon atoms is 1 to 6. Where the number of carbon atoms is not specified, 1 to 20 carbons are intended.

The term "lower alkyl" represents a straight or branched saturated hydrocarbon chain having 1 to 6 carbons.

The term "chemically-feasible" is usually applied to a ring structure present in a compound and means that the ring structure would be expected to be stable by a skilled artisan.

The term "cycloalkyl" or "cycloalkane," as used herein, means an unsubstituted or substituted, saturated, stable, non-aromatic, chemically-feasible carbocyclic ring, having, preferably, from three to fifteen carbon atoms, more preferably, from three to eight carbon atoms. The cycloalkyl carbon ring radical is saturated and may be fused, for example, benzofused, with one to two cycloalkyl, aromatic, heterocyclic or heteroaromatic rings. The cycloalkyl may be attached at any endocyclic carbon atom that results in a stable structure. Preferred carbocyclic rings have from five to six carbons. Examples of cycloalkyl radicals include cyclopropyl, cyclobutyl, cyclopentyl, cyclohexyl, cycloheptyl, and the like.

The term "heterocycloalkyl" refers to a cycloalkyl group which has at least one heteroatom.

The term "halogen" or "Halo" (halogen) is intended to include fluorine, chlorine, bromine or iodine.

The term "alkoxy," as used herein, means an oxygen atom bonded to a hydrocarbon chain, such as an alkyl group (—O-alkyl). Representative alkoxy groups include methoxy, ethoxy and isopropoxy groups.

The term "aryloxy" as used herein, means an oxygen atom bonded to an aryl group (—O-aryl).

The term "fluoroalkyl" represents a straight or branched saturated hydrocarbon chain having the designated number of carbon atoms, substituted with one or more fluorine atoms. Where the number of carbon atoms is not specified, 1 to 20 carbons are intended "Aryl" refers to a mono- or bicyclic ring system having one or two aromatic rings including, but not limited to, phenyl, naphthyl, indenyl, tetrahydronaphthyl, indanyl, anthracenyl, fluorenyl and the like. The aryl group can be unsubstituted or substituted with one, two, or three substituents independently selected from lower alkyl, halo, cyano, nitro, haloalkyl, hydroxy, alkoxy, carboxy, carboxyalkyl, carboxamide, mercapto, sulfhydryl, amino, alkylamino, dialkylamino, sulfonyl, sulfonamido, aryl and heteroaryl.

The term "arylalkyl" refers to an aryl group bonded directly to a subject structure through an alkyl group.

The term "heteroatom," as used herein, means a nitrogen, sulfur, or oxygen atom. Multiple heteroatoms in the same group may be the same or different. The term "heteroalkyl" refers to an alkyl group which has at least one heteroatom.

The term "heteroalkyl" refers to an alkyl group which has at least one heteroatom. Representative examples include alcohols, alkoxyalkyls and alkylaminoalkyls.

The term "heterocycle" or "heterocyclic ring" is defined by all non-aromatic, heterocyclic rings of 3–7 atoms containing 1–3 heteroatoms selected from N, O and S, such as oxirane, oxetane, tetrahydrofuran, tetrahydropyran, pyrrolidine, piperidine, piperazine, tetrahydropyridine, tetrahydropyrimidine, tetrahydrothiophene, tetrahydrothiopyran, morpholine, hydantoin, valerolactam, pyrrolidinone, and the like.

The term "heterocyclic acidic functional group" is intended to include groups such as, pyrrole, imidazole, triazole, tetrazole, and the like.

"Heteroaryl" refers to 5- or 10-membered single or benzofused aromatic rings consisting of 1 to 3 heteroatoms independently selected from the group consisting of —O—, —S, and —N=, provided that the rings do not possess adjacent oxygen and/or sulfur atoms. The heteroaryl group can be unsubstituted or substituted with one, two, or three substituents independently selected from lower alkyl, halo, cyano, nitro, haloalkyl, hydroxy, alkoxy, carboxy, carboxyalkyl, carboxamide, sulfhydryl, amino, alkylamino and dialkylamino. Representative heteroaryl groups include thiazoyl, thienyl, pyridyl, benzothienyl and quinolyl.

The term "heteroarylalkyl" refers to a heteroaryl group bonded directly to a subject structure through an alkyl group.

N-oxides can form on a tertiary nitrogen present in an R substituent, or on =N— in a heteroaryl ring substituent and are included in the compounds of formula I.

The term "prodrug," as used herein, represents compounds that are drug precursors which, following administration to a patient, release the drug in vivo via a chemical or physiological process (e.g., a prodrug on being brought to a physiological pH or through an enzyme action is converted to the desired drug form). A discussion of prodrugs is provided in T. Higuchi and V. Stella, *Pro-drugs as Novel Delivery Systems*, Vol. 14 of A.C.S. Symposium Series (1987), and in *Bioreversible Carriers in Drug Design*, E. B. Roche, ed., American Pharmaceutical Association and Pergamon Press (1987), each of which is incorporated herein by reference in its entirety.

As used herein, the term "composition" is intended to encompass a product comprising the specified ingredients in the specified amounts, as well as any product which results, directly or indirectly, from combination of the specified ingredients in the specified amounts.

The phrase "effective amount," as used herein, means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

As used herein the term "disease" is intended to include any abnormal physical or mental condition, including disorders, as well as any symptoms which are subject evidence of a disease or disorder.

The term "compound having the formula I", and the like as used herein, represents a compound having a chemical structure encompassed by formula I, and includes any and all isomers (e.g., enantiomers, stereoisomers, diastereomers, rotomers, tautomers) and prodrugs of the compound. These compounds can be neutral, acidic or alkaline, and further include their corresponding pharmaceutically-acceptable salts, solvates, esters, and the like.

All isomers of the compounds of the instant invention are contemplated, either in admixture or in pure or substantially pure form. The definition of compounds according to the invention embraces all the possible isomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. Unless noted otherwise, inventive compounds designated with a 1 or 2 above the formula correspond to the first and second isomers, respectively, to elute from a chiral chromatography column during separation from a diastereomeric mixture.

The following solvents and reagents are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); m-chloroperbenzoic acid (MCPBA); triethylamine ($Et_3N$); diethyl ether ($Et_2O$); ethyl chloroformate ($ClCO_2Et$); and 1-(3-dimethylaminopropyl)-3-ethyl carbodiimide hydrochloride (DEC); t-butoxycarbonyl (BOC); phenyl group (Ph); trimethylsilyl isocyanate (TMSNCO); triethylamine (TEA); diethylamine (DEA); di-tert-butyl dicarbonate (BOC)$_2$O;acetyl chloride (AcCl); N-methylmorpholine (NMM); N,N'-dicyclohexylcarbodiimide (DCC); and lithium aluminum hydride (LAH).

As used herein the following terms have the following meanings unless indicated otherwise:

"At least one" means "one or more" preferably 1 to 12, more preferably 1 to 6, most preferably 1, 2 or 3.

"Antineoplastic agent"—means a chemotherapeutic agent effective against cancer;

"Concurrently"—means simultaneously in time; and

"Sequentially"—means administration of one component of a method of treatment involving multi-components, followed by administration of the other component(s); after administration of one component, the second component can be administered substantially immediately after the first component, or the second component can be administered after an effective time period after the administration of the first component; the effective time period is the amount of time given for realization of maximum benefit from the administration of the first component.

Chemotherapeutic Agents

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), Mithramycin, Deoxycoformycin, Mitomycin-C, L-Asparaginase, Interferons-α and β (especially IFN-α), Etoposide, and Teniposide.

Hormonal agents and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin and Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, Navelbene, CPT-11, Anastrazole, Letrazole, Capecitabine, Ralozifine, Droloxifine and Hexamethylmelamine.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

Examples of biological agents useful in the methods of this invention include, but are not limited to, interferon-α, interferon-β and gene therapy.

Microtubule Affecting Agents

As used herein, a microtubule affecting agent is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) Science, 274:2009) estramustine, nocodazole, MAP4, and the like. Examples of such agents are also described in the scientific and patent literature, see, e.g., Bulinski (1997) J. Cell Sci. 110:3055–3064; Panda (1997) Proc. Natl. Acad. Sci. USA 94:10560–10564; Muhlradt (1997) Cancer Res. 57:3344–3346; Nicolaou (1997) Nature 387:268–272; Vasquez (1997) Mol. Biol. Cell. 8:973–985; Panda (1996) J. Biol. Chem. 271:29807–29812.

Particularly preferred microtubule affecting agents are compounds with paclitaxel-like activity. These include, but are not limited to paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) Oncology, 6: 17–23, Horwitz (1992) Trends Pharmacol. Sci. 13: 134–146, Rowinsky (1990) J. Natl. Canc. Inst. 82: 1247–1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:37–47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

In a preferred embodiment, compounds with possible tubulin polymerization activity are screened in vitro. The compounds are screened against cultured WR21 cells (derived from line 69-2 wap-ras mice) for inhibition of proliferation. and/or for altered cellular morphology, in particular for microtubule compaction. In vivo screening of positive-testing compounds can then be performed using nude mice bearing the WR21 tumor cells. Detailed protocols for this screening method are described by Porter (1995) Lab. Anim. Sci., 45(2):145–150.

Other methods of screening compounds for desired activity are well known to those of skill in the art. Typically, these involve assays for inhibition of microtubule assembly and/or disassembly. Assays for microtubule assembly are described, for example, by Gaskin et al. (1974) J. Molec. Biol., 89: 737–758. U.S. Pat. No. 5,569,720 also provides in vitro and in vivo assays for compounds with paclitaxel-like activity.

Methods for the safe and effective administration of the above-mentioned microtubule affecting agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

One aspect of the present invention relates to a pharmaceutical composition comprising a compound of formula (I) in combination or association with a pharmaceutically acceptable carrier or diluent.

Preferably for compounds of the Formula (I), $R^1$ is selected from aryl such as, for example, phenyl and heteroaryl such as, for example, pyridyl, napthyl, imidazolyl, thiazolyl, thienyl, benzothienyl, furanyl, benzofuranyl, quinolinyl, isoquinolinyl, and indolyl, each optionally substituted with one to six groups selected from the following:

a) halogen, e.g. Cl, F, Br, I;
b) —$OCF_3$;
c) —$CF_3$;
d) —CN;
e) (C1–C20)alkyl or $R^{18}$—(C1–C20)alkyl;
f) heteroalkyl, e.g. $NHR^{11}$ or $R^{18}$-heteroalkyl;
g) aryl or $R^{18}$-aryl;
h) heteroaryl or $R^{18}$-heteroaryl;
i) arylalkyl, e.g. benzyl, or $R^{18}$-arylalkyl;
j) heteroarylalkyl or $R^{18}$-heteroarylalkyl;
k) hydroxy;
l) alkoxy;
m) aryloxy;
n) —$SO_2$-alkyl;
o) —$NR^{11}R^{12}$;
p) —$N(R^{11})C(O)R^{13}$,
q) methylenedioxy;
r) difluoromethylenedioxy;
s) trifluoroalkoxy, e.g. —O—(C1–C20)alkyl$CF_3$;
t) —$SCH_3$; and
u) —$SO_2CF_3$;

$R^4$, $R^5$, $R^7$ and $R^8$ are each independently selected from H, alkyl, heteroalkyl, aryl, cycloalkyl, arylalkyl, heteroaryl, heteroarylalkyl, heterocycloalkyl, $OR^{14}$, $NR^{11}R^{12}$,

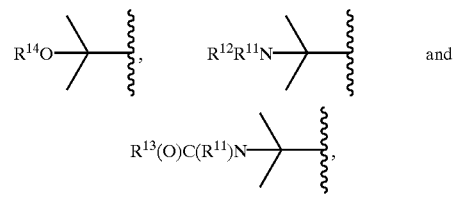

provided that when Z and/or X is N then $R^4$, $R^5$, $R^7$ and $R^8$ are not $OR^{14}$ or $NR^{11}R^{12}$;

$R^{11}$ is selected from H and alkyl;

Z is C; and n=1–3

In a more preferred embodiment, are compounds of the Formula (I) wherein, $R^1$ is selected from aryl and heteroaryl, each optionally substituted with one to six groups selected from following:

a) halogen;
b) —$OCF_3$;
c) —$CF_3$;
d) trifluoroalkoxy;
e) (C1–C6)alkyl or $R^{18}$—(C1–C6)alkyl;
f) heteroalkyl or $R^{18}$-heteroalkyl;
g) aryl or $R^{18}$-aryl;
h) arylalkyl or $R^{18}$-arylalkyl;
i) heteroarylalkyl or $R^{18}$-heteroarylalkly; and
j) alkoxy;

$R^4$, $R^5$, $R^7$ and $R^8$ are each independently selected from the following: H, $OR^{14}$, $NR^{11}R^{12}$, alkyl, aryl, cycloalkyl, arylalkyl, heteroalkyl, heteroarylalkyl, heterocycloalkyl,

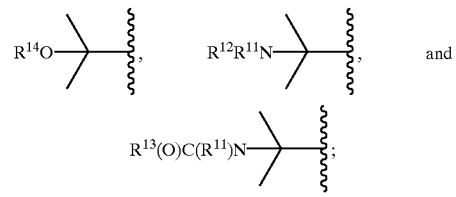

provided that when Z and/or X is N, then $R^4$, $R^5$, $R^7$ and $R^8$ are not $OR^{14}$ or $NR^{11}R^{12}$;

$R^{11}$ is selected from H and alkyl;

Z is C; and n=1–3

Even more preferred are compounds of the Formula (I) wherein, $R^1$ is selected from aryl and heteroaryl, each optionally substituted with one to six groups selected from the following:
a) halogen;
b) —OCF$_3$;
c) —CF$_3$;
d) alkoxy;
e) trifluoroalkoxy; and
f) (C1–C6)alkyl or $R^{18}$—(C1–C6)alkyl;

$R^2$ and $R^3$ are each independently selected from the following: H, alkyl, and heteroalkyl;

$R^4$, $R^5$, $R^7$ and $R^8$ are each independently selected from the following: H, alkyl, heteroalkyl, aryl, cycloalkyl, arylalkyl, heteroaryl, heteroarylalkyl, heterocycloalkyl, OR$^{14}$, NR$^{11}$R$^{12}$,

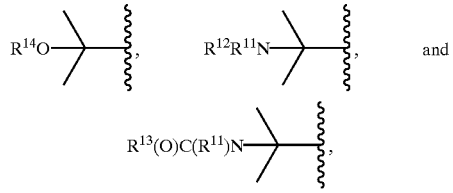

provided that when Z and/or X is N, then $R^4$, $R^5$, $R^7$ and $R^8$ are not OR$^{14}$ or NR$^{11}$R$^{12}$;

$R^{11}$ is selected from H and alkyl;

Z is C.

Yet even more preferred are compounds of the Formula (I) wherein, $R^1$ is selected from aryl and heteroaryl, each optionally substituted with one to six groups selected from the following:
a) halogen;
b) —OCF$_3$;
c) —CF$_3$;
d) alkoxy; and
e) trifluoroalkoxy;

$R^2$ is alkyl;

$R^3$ is H;

$R^4$ and $R^5$ are each independently selected from the following: H, (C1–C6)alkyl, heteroalkyl and

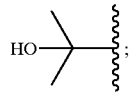

$R^7$ is selected from the following: H, NR$^{11}$R$^{12}$, OR$^{14}$ and alkyl, provided that when X is N, then $R^7$ is not OR$^{14}$ or NR$^{11}$, R$^{12}$;

$R^8$ is selected from the following: H, alkyl, aryl and heteroaryl, which may each be substituted;

$R^{11}$ is selected from H and alkyl; and

Z is C.

Most preferred are compounds of the Formula (1) wherein, $R^1$ is selected from phenyl and pyridyl, each optionally substituted with one to six groups selected from the following:
a) Br, F or Cl;
b) —OCF$_3$;
c) —CF$_3$;
d) methoxy;
e) ethoxy;
f) cyclopropylmethoxy; and
g) —OCH$_2$CF$_3$;

$R^2$ is selected from the following: methyl, ethyl, propyl, cyclopropylmethyl and t-butyl;

$R^3$ is H;

$R^4$ and $R^5$ are each independently selected from the following: H, methyl, ethyl, isopropyl, and t-butyl;

$R^7$ is selected from the following: H, OR$^{14}$ and alkyl;

$R^8$, $R^9$, $R^{10}$, $R^{11}$, $R^{12}$ and $R^{14}$ are each independently selected from H and alkyl;

$R^{13}$ is alkyl;

$R^{15}$ is selected from the following: NR$^{16}$R$^{17}$, OR$^{16}$ and alkyl;

$R^{16}$ and $R^{17}$ are each independently selected from H and alkyl, provided that when $R^{15}$ is OR$^{16}$, then $R^{16}$ is not H; and Z is C.

Illustrative compounds of Formula (I) are shown below in Table A, where the compound numbers S1, S2, etc. are independent of the numbering used in the Example section.

TABLE A

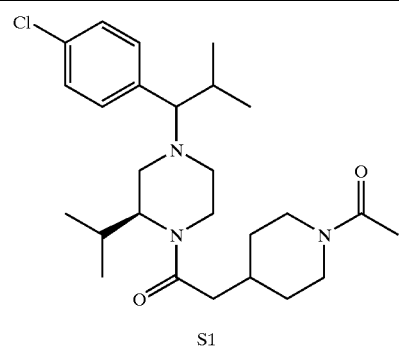

S1

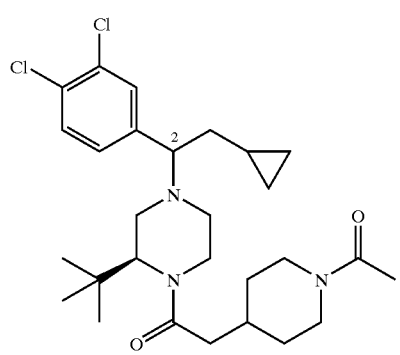

S2

TABLE A-continued
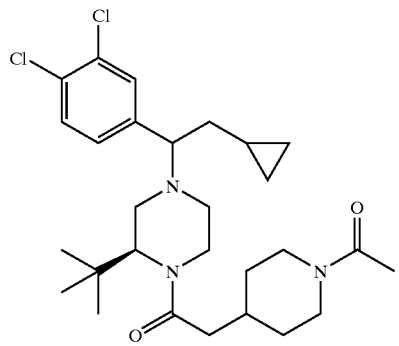
S3
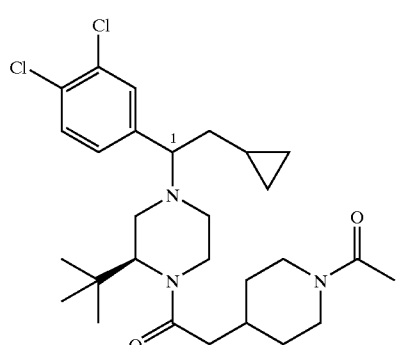
S4
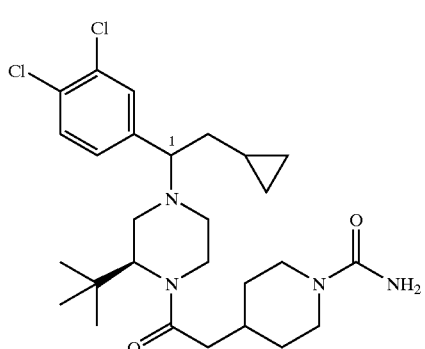
S5
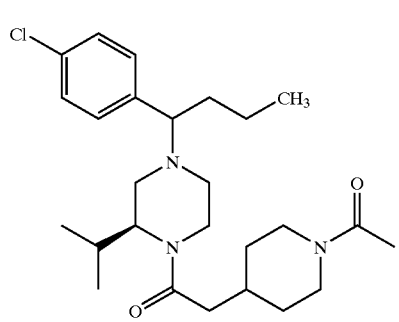
S6
TABLE A-continued
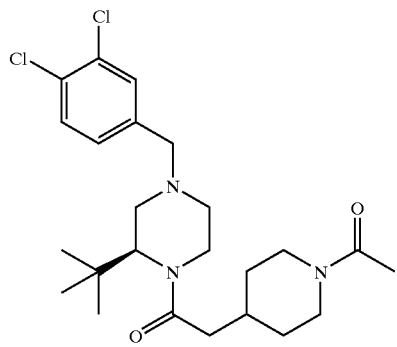
S7
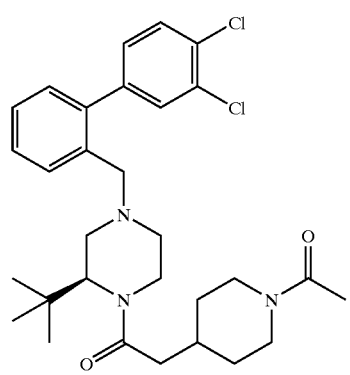
S8
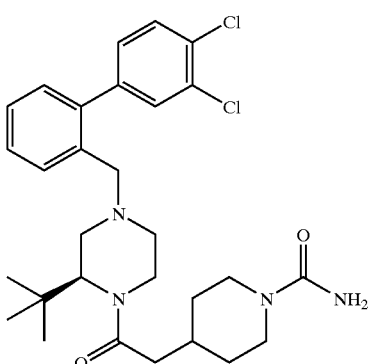
S9
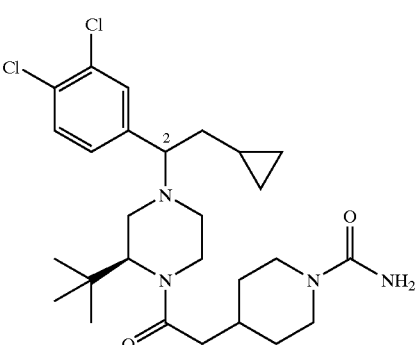
S10

TABLE A-continued
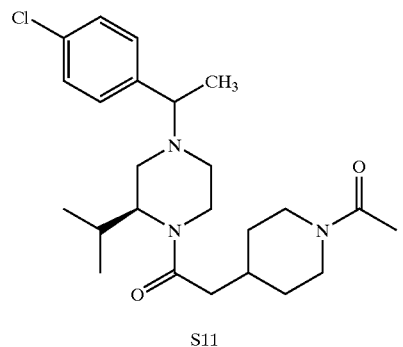
S11
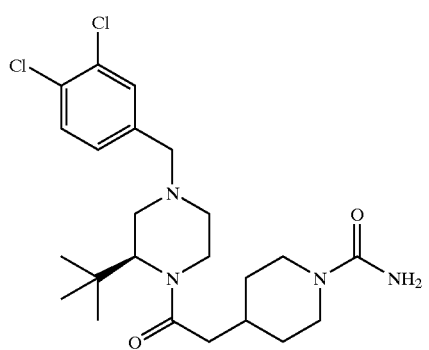
S12
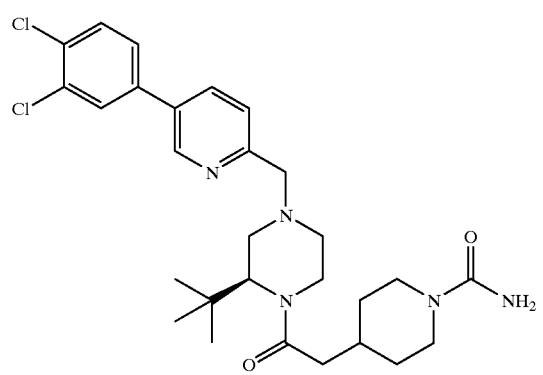
S13
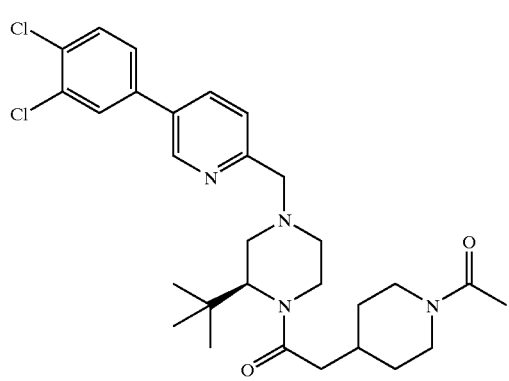
S14
TABLE A-continued
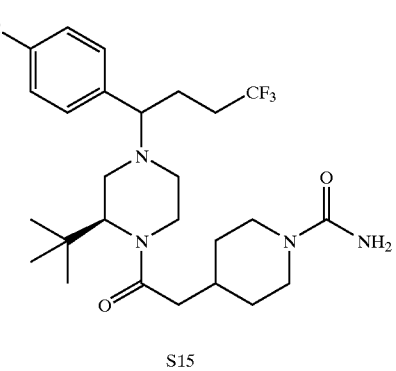
S15
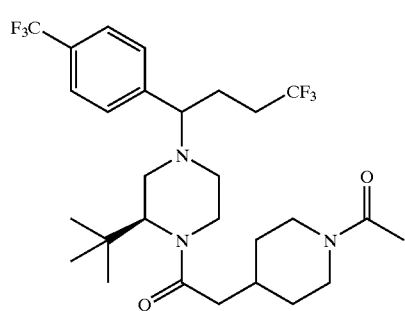
S16
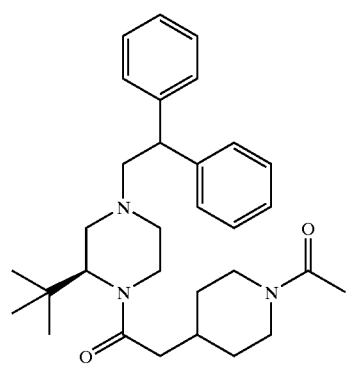
S17
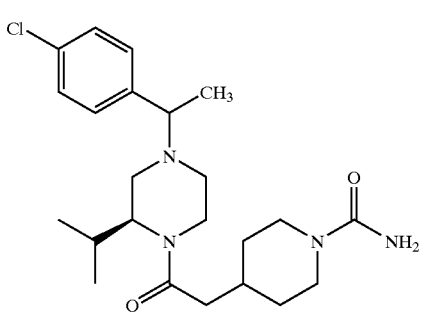
S18
and TABLE A-continued

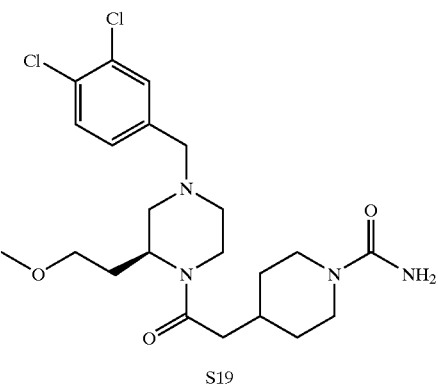

S19

Preferred are compounds represented by the following numbers from Table A above: S1, S2, S3, S4, S5, S6, S7, S8, S9, S10, S11, S12, S13, S14, S15, S16 and S17.

More preferred are compounds represented by the following numbers from Table A above: S1, S2, S3, S4, S5, S6, S7, S8, S9 and S10.

Most preferred are compounds represented by the following numbers from Table A above: S1, S2, S3, S4, S5 and S6.

For compounds of the invention having at least one asymmetrical carbon atom, all isomers, including diastereomers, enantiomers and rotational isomers are contemplated as being part of this invention. The invention includes d and l isomers in both pure form and in admixture, including racemic mixtures. Isomers can be prepared using conventional techniques, or by separating isomers of a compound of formula I.

Compounds of formula I can exist in unsolvated and solvated forms, including hydrated forms. In general, the solvated forms, with pharmaceutically acceptable solvents such as water, ethanol and the like, are equivalent to the unsolvated forms for purposes of this invention.

A compound of formula I may form pharmaceutically acceptable salts with organic and inorganic acids or bases. Examples of suitable bases for salt formation include but are not limited to sodium hydroxide, lithium hydroxide, potassium hydroxide, and calcium hydroxide. Also contemplated are salts formed with pharmaceutically acceptable amines such as ammonia, alkyl amines, hydroxyalkylamines, N-methylglucamine and the like. Certain compounds will be acidic in nature, e.g. those compounds which possess a carboxyl or phenolic hydroxyl group. Salts of phenols can be made by heating acidic compounds with any of the above mentioned bases according to procedures well known to those skilled in the art. For purposes of the invention aluminum, gold and silver salts of the compounds are also contemplated. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution, such as dilute aqueous sodium hydroxide, lithium hydroxide, potassium hydroxide, calcium hydroxide, potassium carbonate, ammonia or sodium bicarbonate.

The present invention provides a method of inhibiting type 3 17β-hydroxysteroid dehydrogenase in a mammal, e.g. a human, which comprises administering to a patient in need thereof of an effective amount, i.e. a therapeutically effective amount, of a compound of formula (I), or a pharmaceutically acceptable salt or solvate thereof.

In another aspect, the present invention provides a method of treating or preventing androgen or estrogen dependent diseases in a mammal, e.g. a human, which comprises administering to a patient in need thereof a therapeutically effective amount of a compound of formula (I), or a pharmaceutically acceptable salt or solvate thereof.

In yet another aspect, the present invention provides a method of treating or preventing prostate cancer, and other androgen-dependent neoplasms, benign prostatic hyperplasia, prostatic intraepithelial neoplasia, androgenic alopecia (i.e. pattern baldness in both male and female patients), hirsutism, polycystic ovary syndrome and acne in a mammal, e.g. a human, which comprises administering to a patient in need thereof, a therapeutically effective amount of a compound of formula (I), or a pharmaceutically acceptable salt or solvate thereof.

The present invention also provides a method of treating or preventing androgen-dependent diseases, comprising administering to a mammal (e.g. human) in need thereof an effective amount of a compound of the invention in combination with at least one anti-androgenic agent (i.e. agents that decrease androgen synthesis or activity).

Examples of such agents include, but are not limited to, the following: inhibitors of 5α-reductase type 1 and/or type 2, e.g. finasteride, SKF105,657, LY191,704, LY320,236, dutasteride, Flutamide, nicaltamide, bicalutamide, LHRH agonists e.g. leuprolide and zoladex, LHRH antagonists, e.g. abarelix and cetrorelix, inhibitors of 17α-hydroxylase/C17–20 lyase, e.g. YM116, CB7630 and liarozole; inhibitors of 17β-Hydroxysteroid dehydrogenase type 5 and/or other 17β-Hydroxysteroid dehydrogenase/17β-oxidoreductase isoenzymes, e.g. EM-1404.

Types of androgen or estrogen dependent diseases include, but are not limited to, prostate cancer, benign prostatic hyperplasia, prostatic intraepithelial neoplasia, acne, seborrheas, hirsutism, androgenic alopecia, precocious puberty, adrenal hyperplasia, and polycystic ovarian syndrome, breast cancer, endometriosis and leiomyoma.

This invention further provides a method of treating or preventing benign prostatic hyperplasia, comprising administering an effective amount of a compound of the invention in combination with at least one agent useful in the treatment or prevention of benign prostatic hyperplasia. Examples of such agents include, but are not limited to, alpha-1 adrenergic antagonists, e.g. tamsulosin and terazosin.

This invention also provides a method of treating or preventing hair loss, comprising administering an effective amount of a compound of the invention in combination with at least one anti-alopecia agent (i.e. agents that treat or prevent hair loss). Useful anti-alopecia agents include potassium channel agonists, e.g., minoxidil and KC-516, or 5α-reductase inhibitors, e.g., finasteride and dutasteride.

The present invention also provides a method of treating or preventing proliferative diseases, especially cancers (tumors), comprising administering concurrently or sequentially, (1) an effective amount (e.g., a therapeutically effective amount) of a compound of the invention, described herein, to a mammal (e.g., a human) in need of such treatment in combination with (2) an effective amount of an anti-cancer agent, i.e., a chemotherapeutic agent, biological agent, and/or surgery, (e.g., prostatectomy) and/or radiation therapy (preferably, γ-radiation).

Examples of cancers (i.e. tumors) which may be inhibited or treated with a compound of this invention, alone or in combination with an anti-cancer agent, include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), renal cancers, myeloid leukemias (for example, acute myelogenous leukemia (AML), thyroid follicular cancer, myelodysplastic syndrome (MDS), bladder carcinoma, epidermal carcinoma, melanoma, breast cancer and prostate cancer.

The method of treating proliferative diseases (cancer), according to this invention, includes a method for treating (inhibiting) the abnormal growth of cells, including transformed cells, in a patient in need of such treatment (e.g., a mammal such as a human), by administering, concurrently or sequentially, an effective amount of a compound of this invention and an effective amount of an anti-cancer agent. Abnormal growth of cells means cell growth independent of normal regulatory mechanisms (e.g., contact inhibition or apoptosis), including the abnormal growth of: (1) tumor cells (tumors) expressing an activated ras oncogene; (2) tumor cells in which the ras protein is activated as a result of oncogenic mutation in another gene; and (3) benign and malignant cells of other proliferative diseases.

In preferred embodiments, the methods of the present invention include methods for treating or inhibiting tumor growth in a patient in need of such treatment (e.g., a mammal such as a human) by administering, concurrently or sequentially, (1) an effective amount of a compound of this invention and (2) an effective amount of an antineoplastic/microtubule agent; biological agent; and/or surgery (e.g. prostatectomy) and/or radiation therapy. Examples of tumors which may be treated include, but are not limited to, epithelial cancers, e.g., prostate cancer, lung cancer (e.g., lung adenocarcinoma), pancreatic cancers (e.g., pancreatic carcinoma such as, for example, exocrine pancreatic carcinoma), breast cancers, renal cancers, colon cancers (e.g., colorectal carcinomas, such as, for example, colon adenocarcinoma and colon adenoma), ovarian cancer, and bladder carcinoma. Other cancers that can be treated include melanoma, myeloid leukemias (for example, acute myelogenous leukemia), sarcomas, thyroid follicular cancer, and myelodysplastic syndrome.

Biological Data
17β-Hydroxysteroid Dehydrogenase Inhibition Data
Methods:

To prepare human recombinant type 3 17β-hydroxysteroid dehydrogenase enzyme, HEK-293 cells stably transfected with human 17β-HSD type 3 were cultured to confluency and harvested for enzyme. The cells were suspended in isolation buffer (20 mM $KH_2PO_4$, 1 mM EDTA, 0.25 M Sucrose, 1 mM PMSF, 5 µg/ml pepstatin A, 5 µg/ml antipain and 5 µg/ml leupeptin) to a concentration between $5.0 \times 10^6$ and $1.0 \times 10^7$ cells/ml. The cells were sonicated on ice using a micro-ultrasonic cell disrupter at an output setting of No. 40 for four 10 second bursts. The broken cells were then centrifuged at 100,000×g for 60 min at 4° C., and the resulting pellet was resuspended, aliquoted into microfuge tubes, and stored at −80° C.

To measure conversion of $^{14}$C-androstenedione to $^{14}$C-testosterone, reaction buffer (12.5 mM $KH_2PO_4$, 1 mM EDTA), NADPH cofactor (1 mM final), test compound, 17β-HSD3 enzyme (30 µg protein) and $^{14}$C-androstenedione substrate (100 nM; 2.7 nCi/tube) were added to 13×100 borosilicate glass tubes to a total volume of 0.5 mL/tube. The tubes were placed in a prewarmed 37° C. water bath for 30 minutes. The reaction was then stopped by adding 1 ml of ethyl ether. The tubes were centrifuged for 20 minutes at 3000 rpm at 4° C. in a table top centrifuge and then snap frozen in a dry ice-methanol bath. The ether layer was decanted into another glass tube, and then evaporated to dryness using compressed nitrogen gas. The samples were resuspended in chloroform (20 mL) and spotted onto silica G60 thin layer chromatography plates. $^{14}$C-Androstenedione substrate and $^{14}$C-testosterone product were separated by placing the plates in chloroform:ethyl acetate (3:1). The plates were dried, exposed overnight, scanned and quantitated on a FUJI FLA2000 phosphorimager.

The percent inhibition of 17β-HSD3 activity is the difference between the percent of maximum specific binding ("MSB") and 100%. The percent of MSB is defined by the following equation, wherein "dpm" represents "disintegrations per minute":

$$\% \text{ MSB} = \frac{(\text{dpm of unknown}) - (\text{dpm of nonspecific binding})}{(\text{dpm of total binding}) - (\text{dpm of nonspecific binding})} \times 100$$

The concentration at which a compound having formula I produces 50% inhibition of binding is then used to determine an inhibition constant ("Ki") using the Chang-Prusoff equation.

It will be recognized that the compounds having formula I can inhibit 17β-HSD3 to varying degrees. The compounds useful for practice of the invention exhibit potent affinities to bind 17β-HSD3 as measured by Ki values (in nM). The activities (potencies) for these compounds are determined by measuring their Ki values. The smaller the Ki value, the more active is a compound for inhibiting a particular enzyme.

Compounds of this invention have a range of 17B-Hydroxysteroid dehydrogenase Type 3 binding activity from about 0.010 nM to about >100 nM. Preferably compounds of this invention have a binding activity in the range of about 0.010 nM to 100 nM, more preferably about 0.010 to 50 nM, and most preferably about 0.010 nM to 10 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration.

Such liquid forms include solutions, suspensions and emulsions.

The compounds of the invention may also be deliverable transdermally. The transdermal composition can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of formula (I) will be regulated according to the judgment of the attending clinician (physician) considering such factors as age, condition and size of the patient as well as severity of the disease being treated. A dosage regimen of the compound of formula (I) can be oral administration of from 10 mg to 2000 mg/day, preferably 10 to 1000 mg/day, more preferably 50 to 600 mg/day, in two to four (preferably two) divided doses. Intermittent therapy (e.g., one week out of three weeks or three out of four weeks) may also be used.

The chemotherapeutic agent and/or radiation therapy can be administered in association with the compounds of the present invention according to the dosage and administration schedule listed in the product information sheet of the approved agents, in the Physicians Desk Reference (PDR) as well as therapeutic protocols well known in the art. Table 1.0 below gives ranges of dosage and dosage regimens of some exemplary chemotherapeutic agents useful in the methods of the present invention. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered chemotherapeutic agents (i.e., antineoplastic agent or radiation) on the patient, and in view of the observed responses of the disease to the administered therapeutic agents.

TABLE 1.0

Exemplary Chemotherapeutic Agents Dosage and Dosage Regimens

| | |
|---|---|
| Cisplatin: | 50–100 mg/m² every 4 weeks (IV)* |
| Carboplatin: | 300–360 mg/m² every 4 weeks (IV) |
| Taxotere: | 60–100 mg/m² every 3 weeks (IV) |
| Gemcitabine: | 750–1350 mg/m2 every 3 weeks (IV) |
| Taxol: | 65–175 mg/m2 every 3 weeks (IV) |

*(IV)—intravenously

Anti-androgenic agents, anti-benign prostatic hyperplasia agents, potassium channel agonists and biological agents can be administered in association with the compounds of the present invention according to the dosage and administration schedule listed in the product information sheet of the approved agents, in the Physicians Desk Reference (PDR) as well as therapeutic protocols well known in the art. It will be apparent to those skilled in the art that the administration of the agents can be varied depending on the disease being treated and the known effects of the agents on that disease. Also, in accordance with the knowledge of the skilled clinician, the therapeutic protocols (e.g., dosage amounts and times of administration) can be varied in view of the observed effects of the administered agents on the patient, and in view of the observed responses of the disease to the administered therapeutic agents.

Compounds of formula (I) may be produced by processes known to those skilled in the art in the following reaction schemes and in the preparations and examples below.

Scheme 1

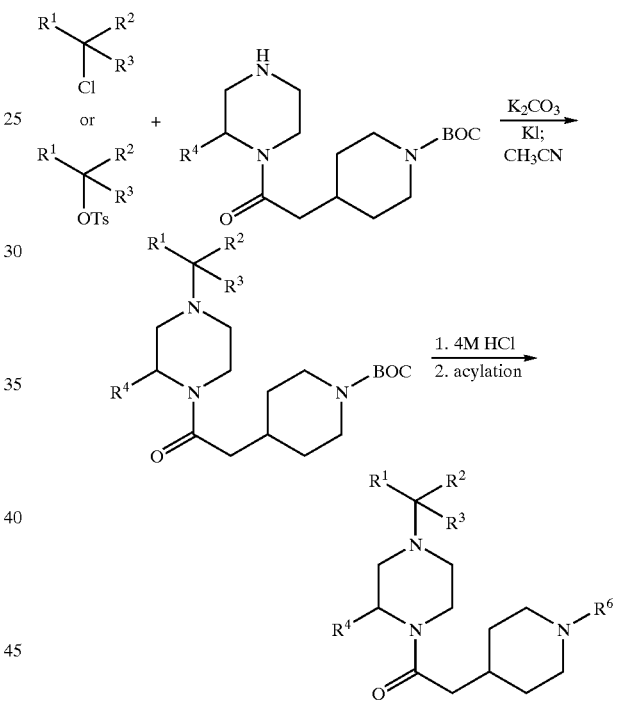

As shown in Scheme 1 above, the piperazine-piperidine core is added to an appropriate chloride. Deprotection and acylation gives the desired product.

Scheme 2

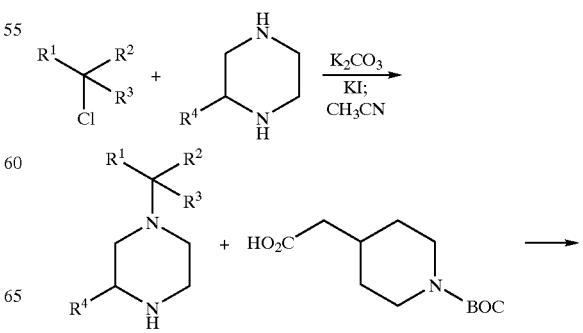

25

-continued

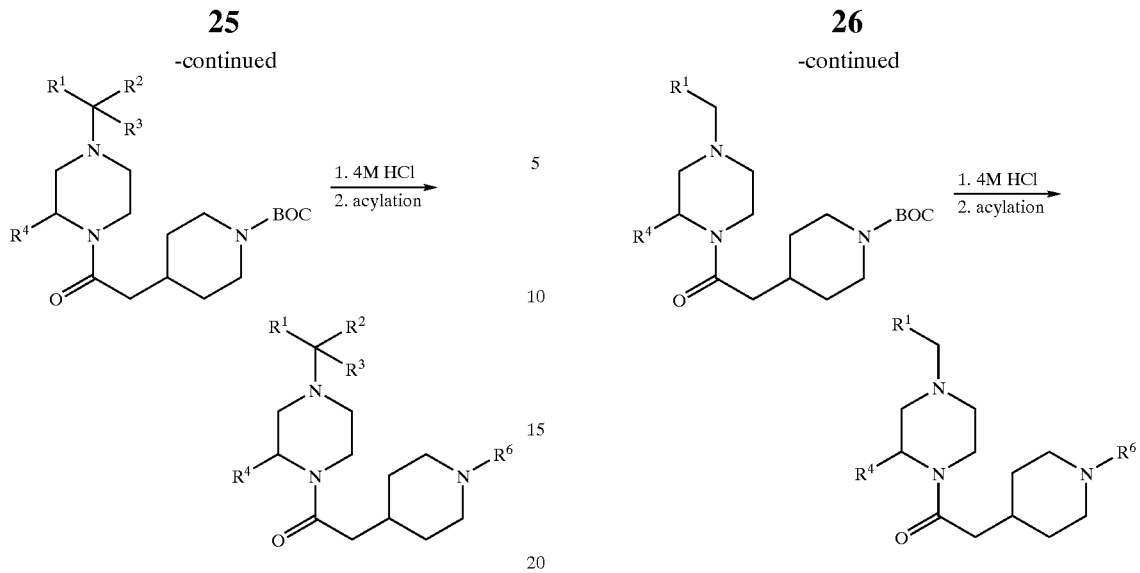

Alternatively, for those more sterically encumbered piperazines, direct coupling is successful in giving the regiochemically desired product (see Scheme 2 above).

Scheme 3

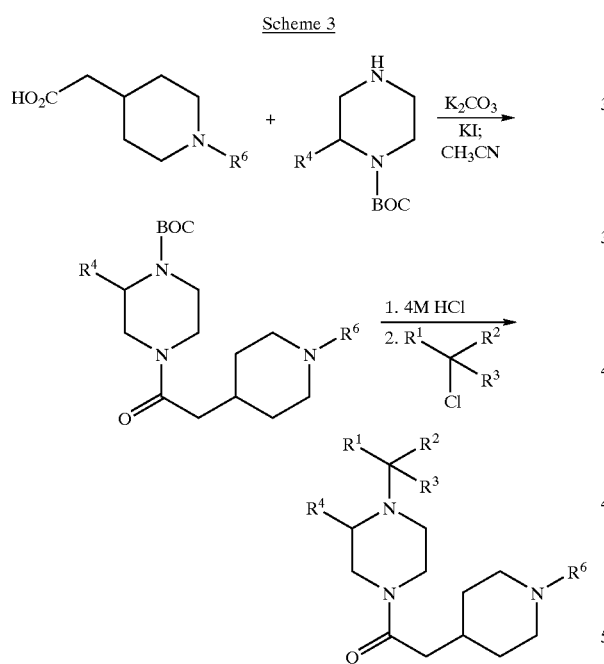

The regiochemical analogs can be prepared through the sequential modification of protecting groups in accordance with Scheme 3 above.

Scheme 4

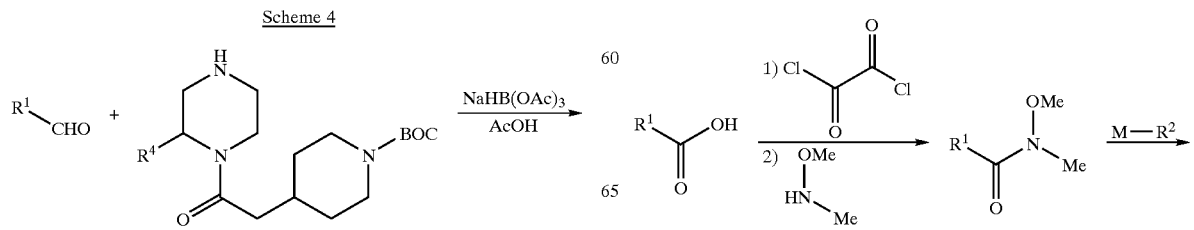

26

-continued

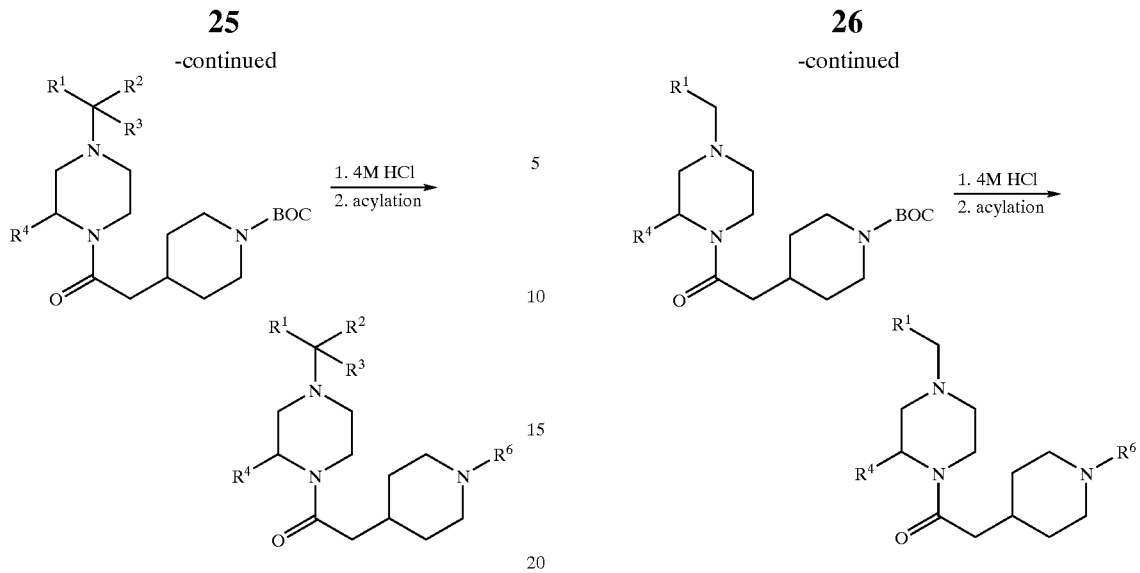

The reductive amination of piperazine-piperidine core, followed by deprotection and acylation, gives the desired product as shown in Scheme 4 above.

Scheme 5

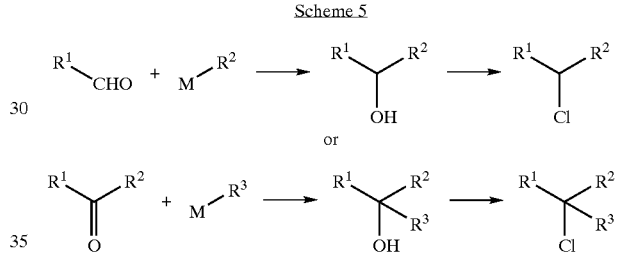

The synthesis of desired chlorides can be accomplished by the addition of an appropriate organometallic to an appropriate aldehyde or ketone (see Scheme 5 above). The resulting alcohol is then converted to the requisite chloride under standard conditions.

Scheme 6

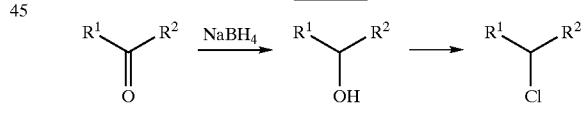

Alternatively, the synthesis of desired chlorides can be accomplished by the reduction of an appropriate ketone, as shown in Scheme 6 above. The resulting alcohol is then converted to the requisite chloride under standard conditions.

Scheme 7

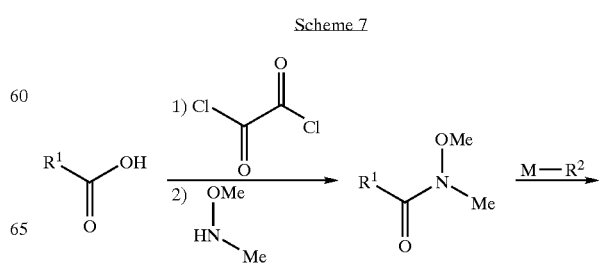

-continued

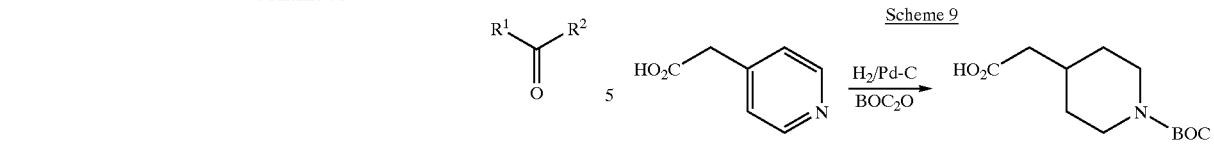

Scheme 9

The synthesis of desired ketone can be accomplished by the addition of an appropriate organometallic to the N,O-dimethylamide, which is converted from an appropriate acid under standard conditions (see Scheme 7 above).

The N-BOC or N-acyl piperidine acetic acid can be prepared as described previously through the reduction of 4-pyridine acetic acid (see Scheme 9 above).

The invention disclosed herein is exemplified by the following preparations and examples which should not be construed to limit the scope of the disclosure. Alternative mechanistic pathways and analogous structures may be apparent to those skilled in the art.

Preparative Example 1

Scheme 8

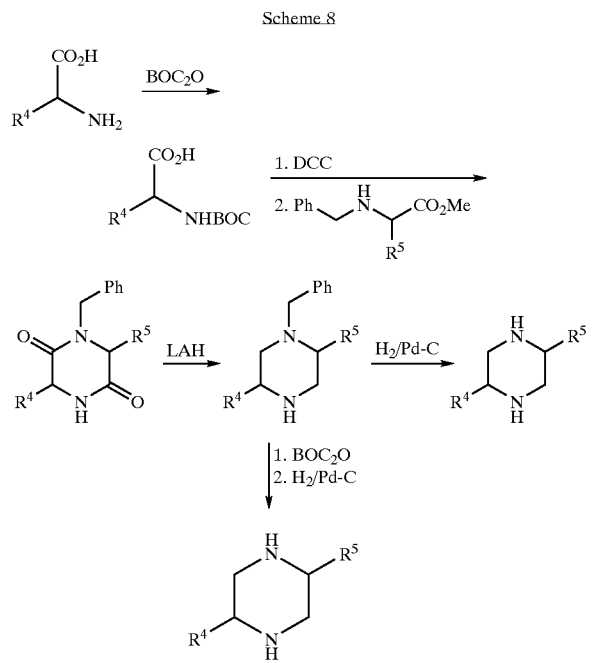

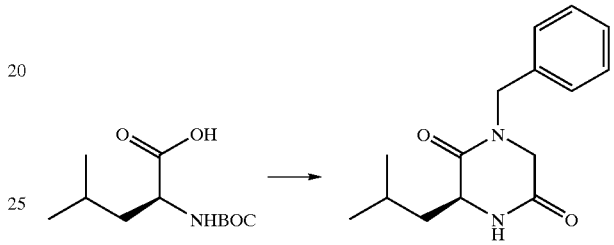

The substituted piperazines can be prepared through the reduction of commercially available diketopiperazines or alternatively from the desired amino acids, as shown in Scheme 8 above.

To a solution of DCC (43.2 mL, 1.0 M in $CH_2Cl_2$, 1.0 eq.) in $CH_2Cl_2$ (200 mL) at 0° C. was added N-t-BOC-L-leucine (10 g, 43.2 mmol). To the resulting slurry was added ethyl N-benzylglycinate (8.1 mL, 1.0 eq.) over 15 minutes. The resulting solution was stirred at 0° C. for 2 hours and room temperature for 1 hour, filtered and then concentrated to give an oil (20.7 g, LCMS: $MH^+$=407). The intermediate was dissolved in $CH_2Cl_2$ (150 mL) through which HCl (g) was bubbled for 4 hours. The solution was purged with $N_2$ and concentrated under reduced pressure. The residue was neutralized with saturated $NaHCO_3$ and extracted with EtOAc (3×200 mL). The combined organics were washed with water, dried over $Na_2SO_4$, filtered and concentrated to give a solid which was used without further purification (11.3 g, 100% yield). LCMS: $MH^+$=261.

Preparative Example 2–4

By essentially the same procedure set forth in Preparative Example 1 substituting the amino acids from Table 1, Column 2, the title compounds in Table 1, Column 3, were prepared:

TABLE 1

| Prep. Ex. | Column 2 | Column 3 | Phys. data |
|---|---|---|---|
| 2 | (structure) | (structure) | LCMS: $MH^+$ = 261 |

TABLE 1-continued

| Prep. Ex. | Column 2 | Column 3 | Phys. data |
|---|---|---|---|
| 3 | (structure: Boc-tert-leucine) | (structure: 1-benzyl-3-tert-butyl-2,5-piperazinedione) | LCMS: MH$^+$ = 261 |
| 4 | (structure: Boc-O-methyl-homoserine) | (structure: 1-benzyl-3-(2-methoxyethyl)-2,5-piperazinedione) | LCMS: MH$^+$ = 129 |

Preparative Example 5

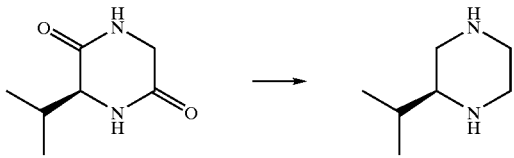

To a solution of (S)-3-isopropyl-2,5-piperazinedione (5.0 g, 32 mmol) in THF (100 ml) at 0° C. was added LAH (137 mL, 1.0 M in THF, 4.3 eq.) dropwise. After the addition was complete, the resulting solution was heated to reflux overnight. The reaction mixture was cooled to room temperature and quenched by the slow, sequential addition of water (5.23 mL), 1N NaOH (5.23 mL), and water (5.23 mL). The resulting slurry was diluted with EtOAc and filtered through a plug of Celite. The residue was washed with EtOAC (4×100 mL) and the combined organics concentrated under reduced pressure. The crude product was purified by flash chromatography using a gradient of 5% MeOH, 10% MeOH, 5% (10% NH$_4$OH) in MeOH, 10% (10% NH$_4$OH) in MeOH, and 20% (10% NH$_4$OH) in MeOH in CH$_2$Cl$_2$ to give a solid (3.03 g, 74% yield). LCMS: MH$^+$=129.

Preparative Examples 6–9

By essentially the same procedure set forth in Preparative Example 5 substituting the piperazinediones (column 2) from Preparative Examples 1–4, the compounds in column 3 were prepared:

TABLE 2

| Prep. Ex. | Column 2 | Column 3 | Phys. data |
|---|---|---|---|
| 6 | (structure: 1-benzyl-3-isobutyl-2,5-piperazinedione) | (structure: 1-benzyl-3-isobutylpiperazine) | LCMS: MH$^+$ = 233 |

TABLE 2-continued

| Prep. Ex. | Column 2 | Column 3 | Phys. data |
|---|---|---|---|
| 7 | | | LCMS: MH$^+$ = 233 |
| 8 | | | LCMS: MH$^+$ = 233 |
| 9 | | | FABMS: MH$^+$ = 235 |

Preparative Example 10

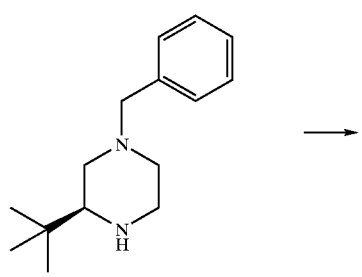

To a solution of N-Boc-4-piperidineacetic acid (prepared as described in U.S. Pat. No. 5,874,442; 35.0 g, 144 mmol) and TEA (20.0 mL, 1.0 eq.) in toluene (100 mL) at 0° C. was added trimethylacetyl chloride (17.7 mL, 1.0 eq.). The resulting slurry was stirred at 0° C. for 1.5 hours before adding the product from Preparative Example 9 (33.5 g, 151 mmol, 1.05 eq.) in toluene (100 mL) and the resulting solution was warmed to room temperature and stirred overnight. The reaction mixture was neutralized by the addition of 1N NaOH and extracted with EtOAc. The combined organics were dried over Na$_2$SO$_4$, filtered, and concentrated. The crude product was purified by flash chromatography using a 50:50 EtOAc:Hexanes solution as eluent (34.4 g, 51% yield). LCMS: MH$^+$=458.

Preparative Example 11

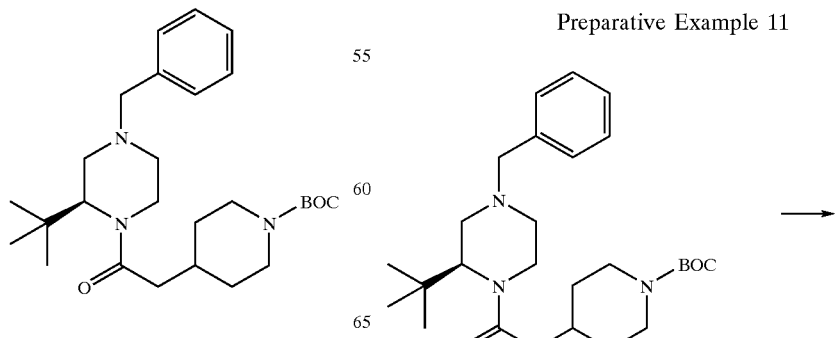

33

-continued

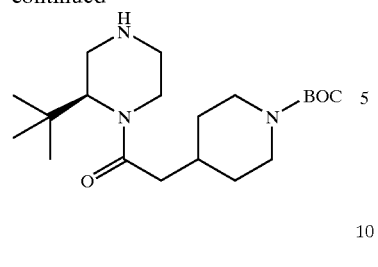

To a solution of the product from Preparative Example 10 (34.0 g, 74.3 mmol) in absolute EtOH (600 mL) was added 10% Pd—C (35.0 g, wet, 50%) and NH$_4$HCO$_2$ (94 g, 10 eq.). The reaction mixture was heated to reflux for 3 hours, cooled to room temperature, filtered through a plug of Celite and concentrated under reduced pressure. The residue was diluted with EtOAc and washed sequentially with H$_2$O, 1N NaOH, H$_2$O, and brine. The organics were dried over Na$_2$SO$_4$, filtered, and concentrated in vacuo. The crude product was purified by flash chromatography using a 5% (10% NH$_4$OH in MeOH) in CH$_2$Cl$_2$ to 10% (10% NH$_4$OH in MeOH in CH$_2$Cl$_2$ as eluent (20 g, 74% yield). LCMS: MH$^+$=368.

Preparative Example 12

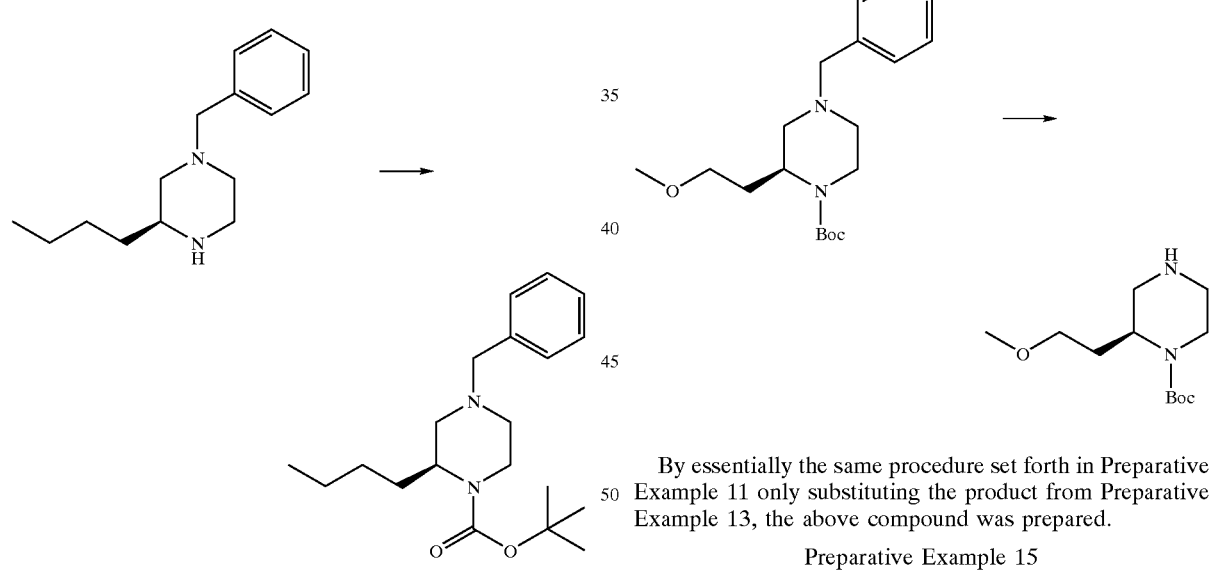

To a solution of the product from Preparative Example 7 (8.2 g, 31.5 mmol) in CH$_2$Cl$_2$ (300 mL) was added (BOC)$_2$O (7.5 g, 1.02 eq.). The resulting solution was stirred at room temperature overnight. The reaction was quenched by the addition of saturated NaHCO$_3$ and separated. The organic layer was washed with brine, dried over Na$_2$SO$_4$, filtered, and concentrated under reduced pressure. The crude product was purified by flash chromatography using a 10% EtOAc in hexanes solution as eluent (10.6 g, 99% yield). LCMS: MH$^+$=333.

34

Preparative Example 13

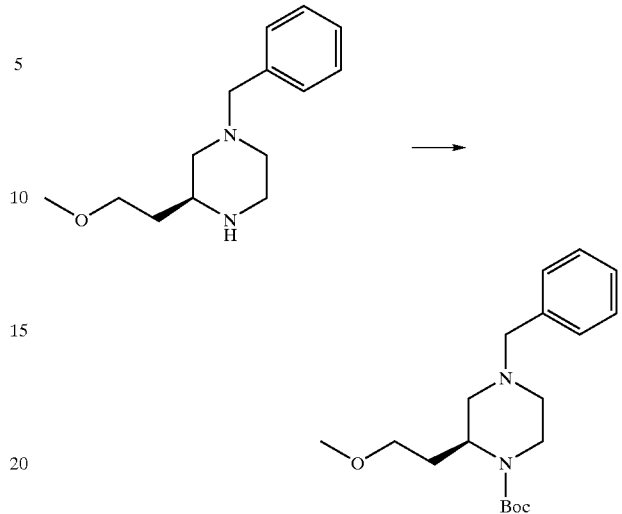

By essentially the same procedure set forth in Preparative Example 12, only substituting the product from Preparative Example 10, the above compound was prepared. LCMS: MH$^+$=335.

Preparative Example 14

By essentially the same procedure set forth in Preparative Example 11 only substituting the product from Preparative Example 13, the above compound was prepared.

Preparative Example 15

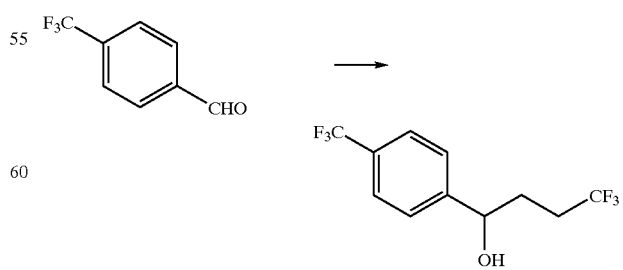

A solution of Mg (1.16 g, 1.6 eq.) and I$_2$ (cat.) in Et$_2$O (48 mL) was treated with 3,3,3-trifluoro-1-iodopropane (8.0 g, 1.2 eq. initially 20% of total) and the resulting solution was heated to reflux to initiate Grignard formation. Following initiation, the remaining 3,3,3-trifluoro-1-iodopropane was added dropwise to maintain a gentle reflux. The reaction mixture was stirred at room temperature an additional hour and transferred via canulae to a solution of 4-trifluorobenzaldehyde (4.1 mL, 30 mmol) in Et$_2$O (95 mL) at 0° C. The resulting solution was stirred at 0° C. for 1 hour and room temperature for 1 hour. The reaction was quenched by pouring it over ice (100 g) and saturated NH$_4$Cl. The resulting solution was extracted with CH$_2$Cl$_2$, the combined organics were dried over Na$_2$SO$_4$, filtered, concentrated and used without further purification.

Preparative Example 16–18

By essentially the same procedure set forth in Preparative Example 15 only substituting the commercial available alkyl magnesium halides in Table 3, column 2 and the arylaldehydes in column 3, the compounds in column 4 were prepared:

by the addition of 1N HCl. The resulting solution was stirred at room temperature 2 hours and extracted with CH$_2$Cl$_2$. The combined organics were dried over Na$_2$SO$_4$, filtered, and concentrated. The crude product was purified by flash chromatography using a 100% hexanes to 10% EtOAc in hexanes solution gradient as eluent (0.10 g, 21% yield). LCMS: MH$^+$=227.

Preparative Example 20

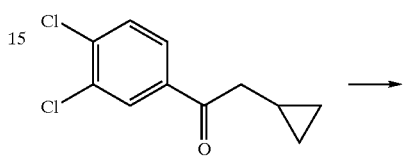

TABLE 3

| Prep Ex. | Column 2 | Column 3 | Column 4 |
|---|---|---|---|
| 16 | Cl-C$_6$H$_4$-CHO | CH$_3$MgCl | Cl-C$_6$H$_4$-CH(OH)CH$_3$ |
| 17 | Cl-C$_6$H$_4$-CHO | (CH$_3$)$_2$CHMgCl | Cl-C$_6$H$_4$-CH(OH)CH(CH$_3$)$_2$ |
| 18 | Cl-C$_6$H$_4$-CHO | BuMgCl | Cl-C$_6$H$_4$-CH(OH)CH$_2$CH$_2$CH$_2$CH$_3$ |

Preparative Example 19

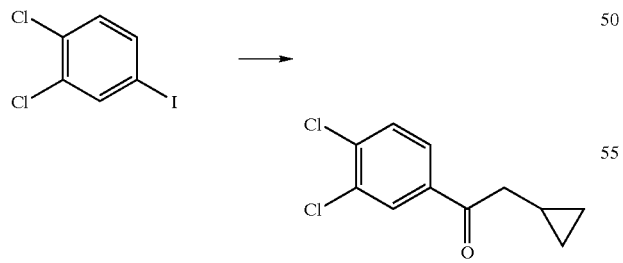

To a solution of 1,2-dichloro-4-iodobenzene (1.0 g, 3.68 mmol) in ether (10 mL) at 0° C. was added iPrMgCl (2.2 mL, 2M in Et$_2$O) dropwise and the resulting solution stirred at 0° C. for 30 minutes and room temperature 1 hour. The reaction mixture was recooled to 0° C. and cyclopropylacetonitrile (0.34 mL, 1.0 eq.) was added. The reaction mixture was stirred at 0° C., room temperature 1 hour, then quenched -continued

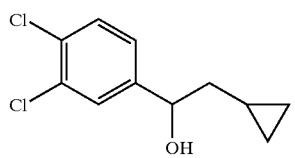

The product from Preparative Example 19 (0.45 g, 1.97 mmol) in THF (5.0 mL) and MeOH (1.0 mL) was stirred at 0° C. with NaBH$_4$ (0.075 g, 1.0 eq.) for 1 hour. The resulting solution was quenched by the addition of water and extracted with CH$_2$Cl$_2$. The combined organics were dried over Na$_2$SO$_4$, filtered, concentrated under reduced pressure and used without further purification.

Preparative Example 21

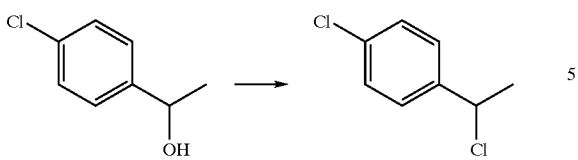

To the product from Preparative Example 16 (1.57 g, 10 mmol) in toluene (5.0 mL) at 0° C. was added SOCl$_2$ (2.39 g, 2.0 eq.) dropwise. The resulting solution was stirred at 0° C. for 1 hour, warmed to room temperature and stirred overnight. The crude reaction mixture was concentrated under reduced pressure to give the above compound which was used without further purification.

Preparative Examples 22–23

By essentially the same procedure as set forth in Preparative Example 21, the compounds in Table 4, Column 3 were prepared from the corresponding alcohols in Column 2.

TABLE 4

| Prep. Ex. | Column 2 | Column 3 |
|---|---|---|
| 22 | Cl-C6H4-CH(OH)-CH(CH3)2 | Cl-C6H4-CH(Cl)-CH(CH3)2 |
| 23 | Cl-C6H4-CH(OH)-CH2CH2CH3 | Cl-C6H4-CH(Cl)-CH2CH2CH3 |

Preparative Example 24

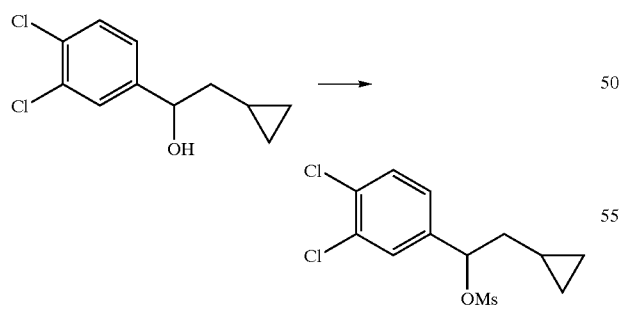

To a solution of the product from Preparative Example 20 (0.48 g, 2.08 mmol) in CH$_2$Cl$_2$ (5 mL) at 0° C. was added Et$_3$N (0.87 mL, 3 eq.), followed by methanesulfonyl chloride (0.306 mL, 1.5 eq.). The reaction mixture was stirred at 0° C. for 1 hour, then quenched by the addition of saturated NaHCO$_3$. The resulting solution was extracted with CH$_2$Cl$_2$. The combined organics were dried over Na$_2$SO$_4$, filtered, and concentrated. The crude product was purified by flash chromatography using a 40:60 EtOAc:Hexanes solution as eluent (0.47 g, 73% yield).

Preparative Example 25

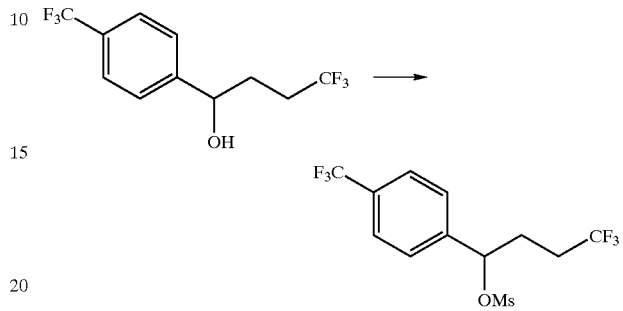

By essentially the same procedure set forth in Preparative Example 24 only substituting the product from Preparative Example 15, the above compound was prepared (0.36 g, 82% yield).

Preparative Example 26

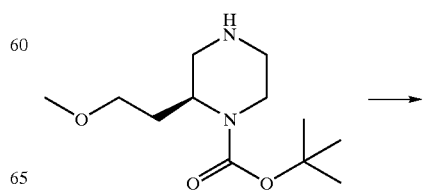

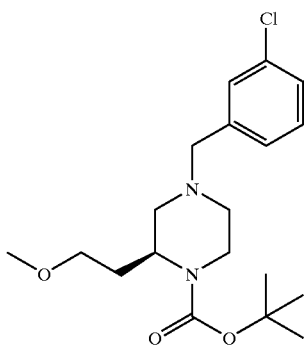

To a solution of the product from Preparative Example 14 (0.25 g, 1.0 mmol) and 3,4-dichlorobenzaldehyde (0.23 g, 1.3 eq.) in $CH_2Cl_2$ (5 mL) was added NaHB$(OAc)_3$ (0.32 g, 1.5 eq.) and AcOH (0.14 mL, 2.4 eq.) and the resulting solution was stirred at room temperature for 96 hours. The reaction mixture was quenched by the addition of saturated $NaHCO_3$ and extracted with $CH_2Cl_2$. The combined organics were dried over $Na_2SO_4$, filtered and concentrated under reduced pressure. The crude product was purified by flash chromatography using a 10% EtOAc in $CH_2Cl_2$ solution as eluent (0.27 g, 66% yield). FABMS: $MH^+=403$.

Preparative Example 27

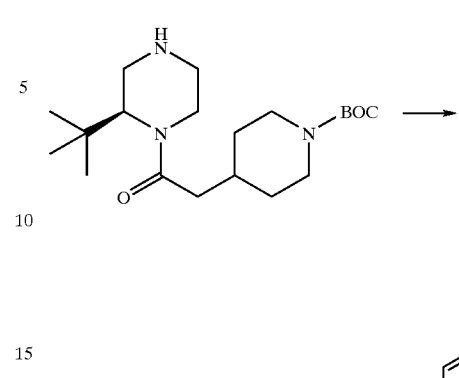

By essentially the same procedure set forth in Preparative Example 26 only substituting the product from Preparative Example 11, the above compound was prepared (0.33 g, 92% yield). LCMS: $MH^+=526$.

Preparative Examples 28–30

By essentially the same procedure as set forth in Preparative Example 27, the compounds in Table 5, Column 3 were prepared from the corresponding aldehydes in Column 2:

TABLE 5

| Prep. Ex. | Column 2 | Column 3 | CMPD |
|---|---|---|---|
| 28 | (2-bromobenzaldehyde) | (2-bromobenzyl piperazine product) | LCMS: $MH^+ = 536$ |
| 29 | (5-bromopyridine-2-carbaldehyde) | (5-bromopyridin-2-ylmethyl piperazine product) | — |

TABLE 5-continued

| Prep. Ex. | Column 2 | Column 3 | CMPD |
|---|---|---|---|
| 30 | diphenylacetaldehyde structure | piperazine-piperidine Boc compound with 2,2-diphenylethyl substituent | LCMS: MH+ = 548 |

Preparative Example 31

[Structure: 2-bromobenzyl piperazine with t-butyl, acyl-piperidine-Boc] → [Structure: 3',4'-dichlorobiphenyl-2-ylmethyl piperazine with t-butyl, acyl-piperidine-Boc]

To a solution of the product from Preparative Example 28 (0.26 g, 0.485 mmol), 3,4-dichlorophenyl boronic acid (0.19 g, 2.0 eq.) and Na$_2$CO$_3$ (0.15 g, 2.0 eq.) in THF:H$_2$O (4:1, 10 mL) was added PdCl$_2$(PPh$_3$)$_2$ (0.034 g, 10 mol %). The resulting solution was heated to reflux overnight. The reaction mixture was cooled to room temperature, quenched by the addition of H$_2$O, and extracted with CH$_2$Cl$_2$. The combined organics were dried over Na$_2$SO$_4$, filtered, and concentrated. The crude product was purified by flash chromatography using a 10:90 EtOAc:CH$_2$Cl$_2$ solution as eluent to yield the product (0.17 g, 58% yield). LCMS: MH$^+$=602.

Preparative Examples 32

[Structure: 5-bromo-2-pyridylmethyl piperazine with t-butyl, acyl-piperidine-Boc] → [Structure: 5-(3,4-dichlorophenyl)-2-pyridylmethyl piperazine with t-butyl, acyl-piperidine-Boc]

By essentially the same procedure set forth in Preparative Example 31, only substituting the product from Preparative Example 29 (0.25 g, 0.465 mmol) the above compound (0.12 g, 43% yield) was prepared. LCMS: MH$^+$=603.

Preparative Examples 33

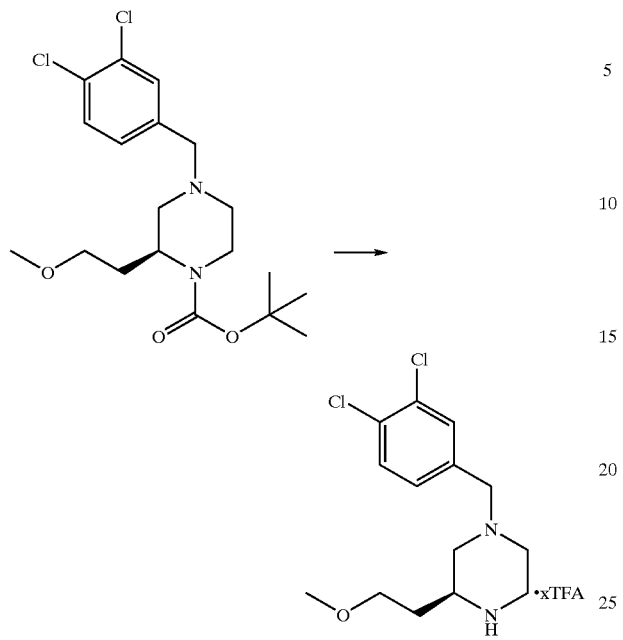

The product from Preparative Example 26 (0.26 g, 0.48 mmol) was stirred at room temperature in TFA (5 mL) for 1 hour. The resulting solution was concentrated under reduced pressure and used without further purification.

Preparative Example 34

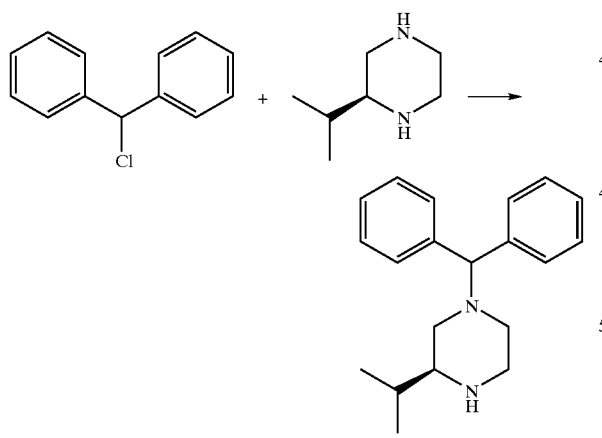

A solution of benzhydryl chloride (5.40 g, 26.6 mmol), the product from Preparative Example 5 (3.4 g, 26.6 mmol) and NaI (0.75 g, 5 mmol) in $CH_3CN$ (40 mL) was heated to reflux overnight. The reaction mixture was cooled to room temperature, quenched by the addition of saturated $NaHCO_3$, and extracted with $CH_2Cl_2$. The combined organics were dried over $Na_2SO_4$, filtered, and concentrated. The crude product was purified by flash chromatography using a 5% MeOH (10% $NH_4OH$) in $CH_2Cl_2$ to yield a solid (4.02 g, 51% yield). LCMS: $MH^+=295$.

Preparative Example 35

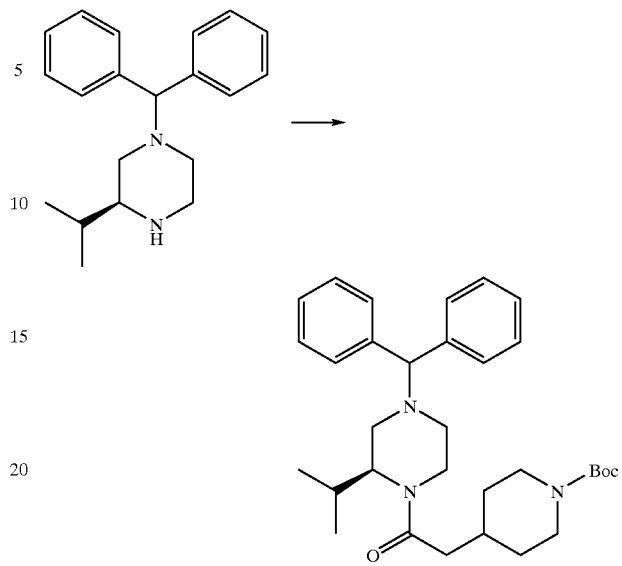

The product from Preparative Example 34 (4.00 g, 13.6 mmol), N-Boc-4-piperadineacetic acid (3.30 g, 13.6 mmol), DEC (3.39 g, 1.3 eq.), HOBt (2.43 g, 1.3 eq.), and NMM (3.54 g, 2.5 eq.) were stirred at room temperature $CH_2Cl_2$ for 1.5 days. The reaction mixture was poured into saturated $NaHCO_3$ and extracted with $CH_2Cl_2$. The combined organics were dried over $Na_2SO_4$, filtered, and concentrated. The crude product was purified by flash chromatography using a 5% MeOH (10% $NH_4OH$) in $CH_2Cl_2$ to yield a solid (6.7 g, 96% yield). LCMS: $MH^+=520$.

Preparative Example 36

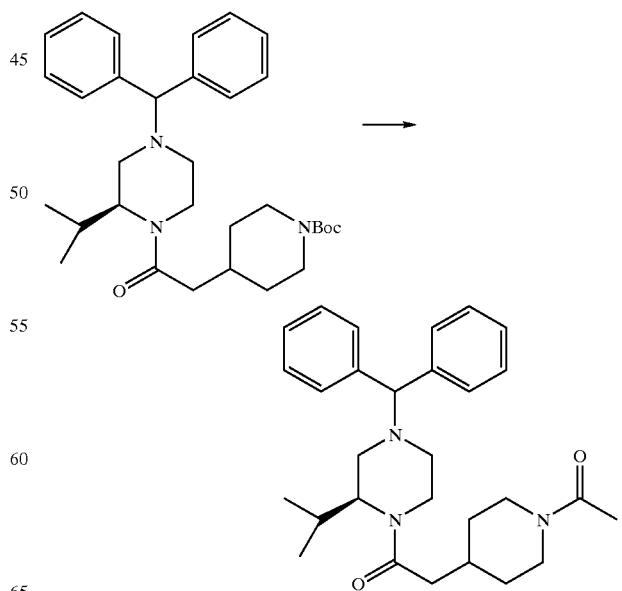

TFA (4.0 mL) was added to a solution of the product from Preparative Example 35 (2.00 g, 3.86 mmol) in anhydrous CH$_2$Cl$_2$ (40 mL) at 0° C. under N$_2$. The mixture was stirred at 0° C. for 15 min, then 16 mL of TFA was added and the stirring was continued for another 30 min at 0° C. The mixture was poured onto solid K$_2$CO$_3$ (50 g), H$_2$O (200 mL) was added, and the mixture was extracted with CH$_2$Cl$_2$ (4×30 mL). The extracts were dried over Na$_2$SO$_4$, filtered, and the solvent was evaporated. The solid was dissolved in anhydrous CH$_2$Cl$_2$ (30 mL), and Ac$_2$O (0.79 g, 7.7 mmol) and TEA (1.95 g, 19.3 mmol) were added. The mixture was stirred under N$_2$ for 24 hrs, poured into sat. NaHCO$_3$ (50 mL), and extracted with CH$_2$Cl$_2$ (2×30 mL). The combined extracts were dried over Na$_2$SO$_4$ and filtered. The residue was purified by flash chromatography using 7% MeOH (10% NH$_4$OH) in CH$_2$Cl$_2$ to give a solid (1.63 g; 92%) LCMS: MH$^+$=462; mp=65–71° C.

Preparative Example 37

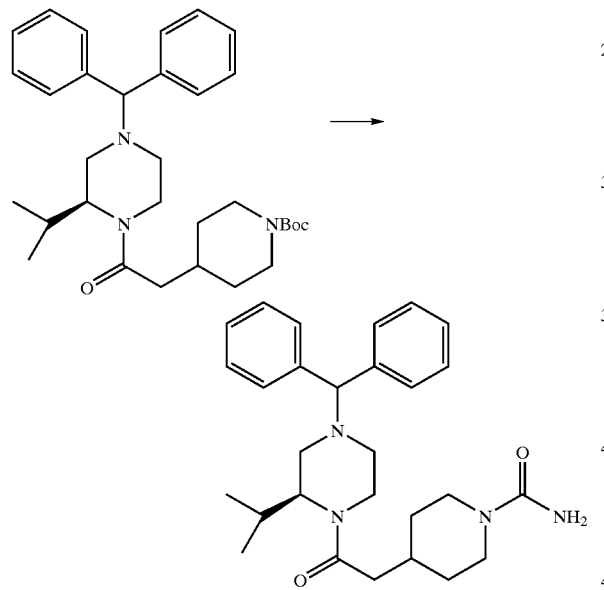

TFA (4.0 mL) was added to a solution of the product from Preparative Example 35 (2.00 g, 3.86 mmol) in anhydrous CH$_2$Cl$_2$ (40 mL) at 0° C. under N$_2$. The mixture was stirred at 0° C. for 15 min, then 16 mL of TFA was added and the stirring was continued for another 30 min at 0° C. The mixture was poured onto solid K$_2$CO$_3$ (50 g), H$_2$O (200 mL) was added and the mixture was extracted with CH$_2$Cl$_2$ (4×30 mL). The extracts were dried over Na$_2$SO$_4$, filtered, and the solvent was evaporated. The solid was dissolved in anhydrous CH$_2$Cl$_2$ (30 mL), and TEA (1.95 g, 19.3 mmol) and TMSNCO (4.44 g, 38.6 mmol) were added. The mixture was stirred under N$_2$ for 3 hrs, poured into sat. NaHCO$_3$ (200 mL), and extracted with CH$_2$Cl$_2$ (2×30 mL). The combined extracts were dried over Na$_2$SO$_4$, filtered, and the solvent was evaporated. The residue was purified by flash chromatography using 11% MeOH (10% NH$_4$OH) in CH$_2$Cl$_2$ to give a solid (1.51 g; 85%). LCMS: MH$^+$=463; mp=100–107° C.

Preparative Example 38

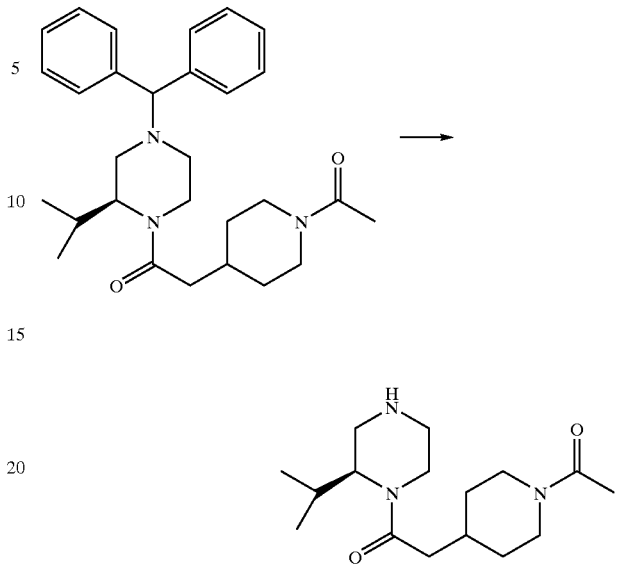

A solution of the product from Example 36 (1.00 g, 2.20 mmol) and HCO$_2$NH$_4$ (2.77 g, 44.0 mmol) in anhydrous MeOH (30 mL) was added under N$_2$ to a suspension of 10% Pd/C (1.17 g) in anhydrous MeOH (20 mL). The mixture was stirred for 16 hrs under N$_2$, poured into 250 CH$_2$Cl$_2$ (250 mL), and filtered through Celite. The solvent was evaporated and the residue was purified by flash chromatography using 11% MeOH (10% NH$_4$OH) in CH$_2$Cl$_2$ to give 555 mg (87%) of a solid.

Preparative Example 39

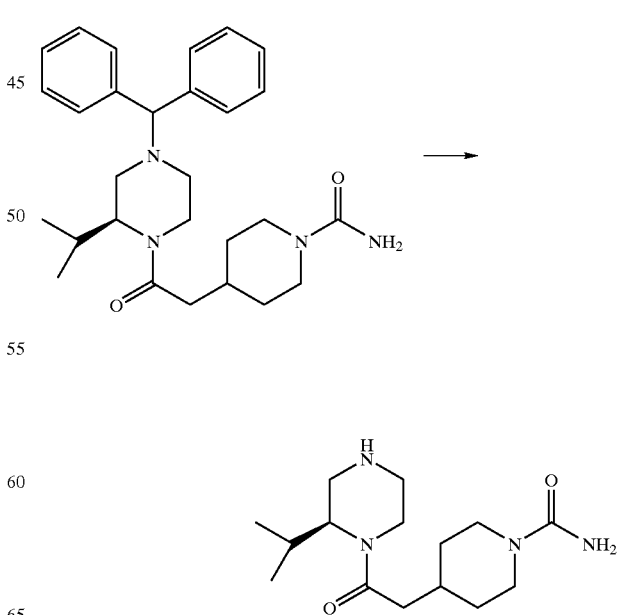

By essentially the same procedure given in Preparative Example 38, 1.00 g (2.20 mmol) of the product from Preparative Example 37 was converted into 520 mg (81%) of the above compound as a solid.

Preparative Example 40

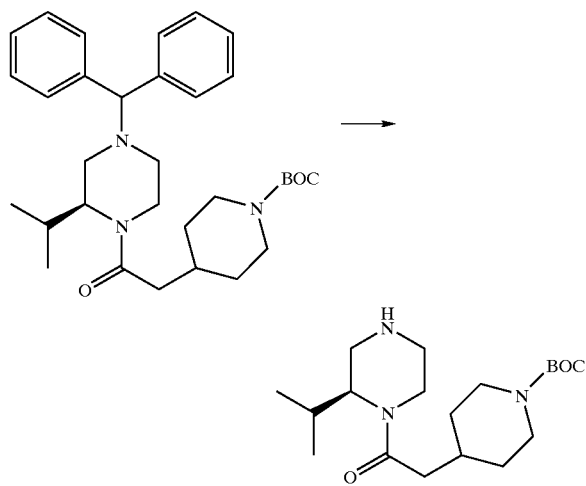

By essentially the same procedure given in Preparative Example 38, the product from Preparative Example 35 was converted into 4.02 g (91%) of the above compound as a wax.

Preparative Example 41

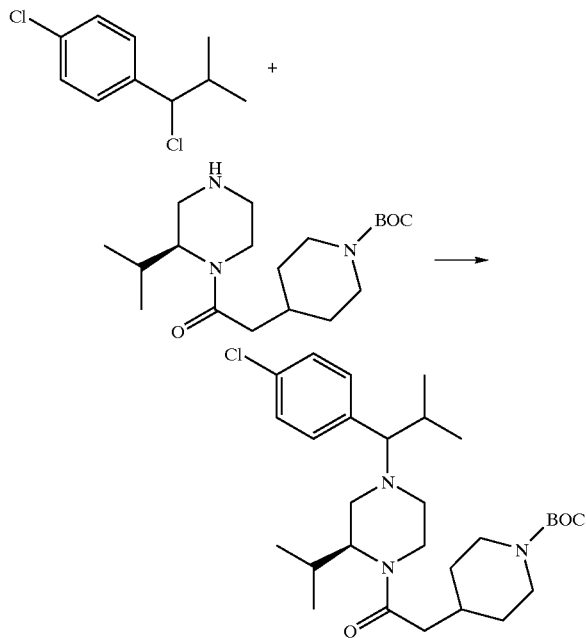

A solution of the product from Preparative Example 22 (0.071 g, 0.35 mmol), the product from Preparative Example 40 (0.1 g, 0.28 mmol), NaI (0.045 g, 0.3 mmol) and $K_2CO_3$ (0.15 g, 1.1 mmol) in $CH_3CN$ (3 mL) was heated to reflux for 2.5 days. The reaction mixture was cooled to room temperature, quenched by the addition of 5% $K_2CO_3$, and extracted with $CH_2Cl_2$. The combined organics were dried over $Na_2SO_4$, filtered, and concentrated. The crude product was purified by flash chromatography using a 3% MeOH (10% $NH_4OH$) in $CH_2Cl_2$ to give a solid (0.029 g, 20% yield). LCMS: $MH^+$=521.

Preparative Example 42

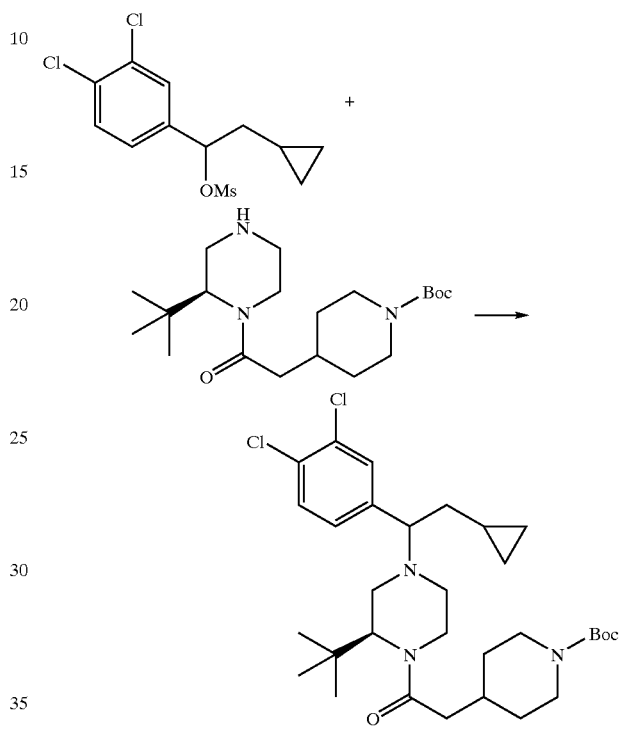

A solution of the products from Preparative Example 11 (0.977 g, 1.75 eq.) and Preparative Example 24 (0.47 g, 1.52 mmol), $K_2CO_3$ (0.525 g, 2.5 eq.), and KI (0.228 g, 1.0 eq.) in $CH_3CN$ (20 mL) was heated to reflux for 24 hours. The reaction mixture was cooled, diluted with saturated $NaHCO_3$, and extracted with EtOAc. The combined organics were dried over $Na_2SO_4$, filtered, and concentrated. The crude product was purified by flash chromatography using a 50:50 Hexanes:EtOAc solution as eluent (0.45 g, 51% yield). LCMS: $MH^+$=580.

Preparative Examples 43 and 44

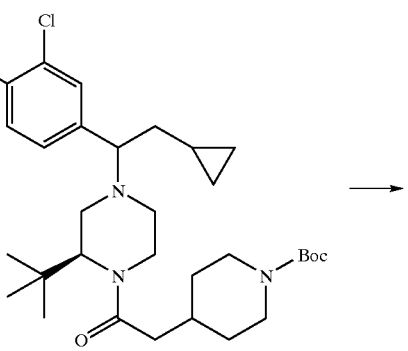

-continued

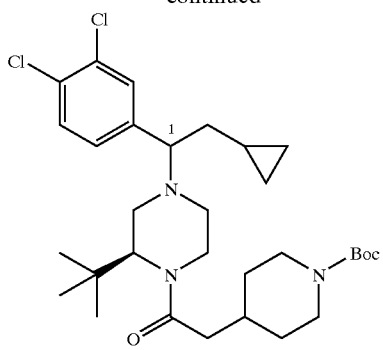

+

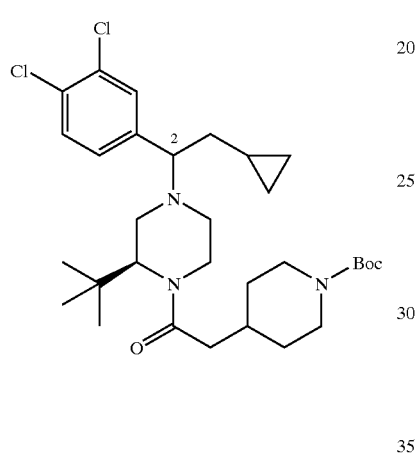

The above compounds were prepared by the separation of diastereomers of the product from Preparative Example 42 by preparative HPLC, using a CHIRALPAK AD column with 98:2 hexanes:IPA with 0.2% DEA as eluent:

Preparative Example 43 (first eluting isomer): LCMS: MH$^+$=580.

Preparative Example 44 (second eluting isomer): LCMS: MH$^+$=580.

Preparative Example 45

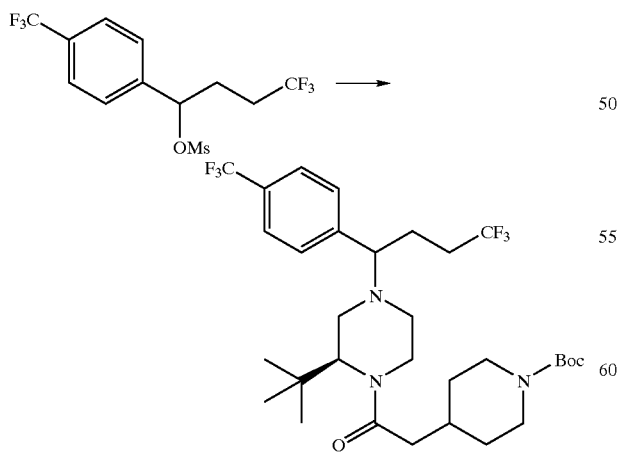

By essentially the same procedure set forth in Preparative Example 42 only substituting the product from Preparative Example 25, the above compound was prepared (0.3 g, 32% yield) LCMS: MH$^+$=622.

Preparative Example 46

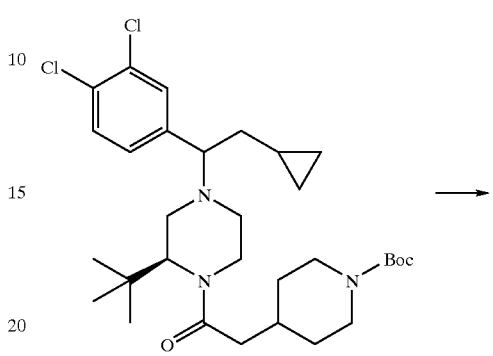

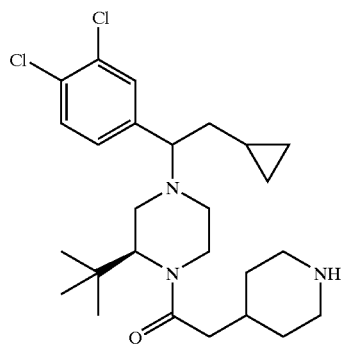

A solution of the product from Preparative Example 42 (0.15 g, 0.26 mmol) in 4 M HCl in dioxane (5 mL) was stirred at room temperature for 2 hours. The resulting solution was concentrated under reduced pressure. The residue was dissolved in CH$_2$Cl$_2$, neutralized by the addition of 1N NaOH and separated. The organics were dried over Na$_2$SO$_4$, filtered and concentrated to give a solid (0.12 g, 96% yield) which was used without further purification LCMS: MH$^+$=480.

Preparative Examples 47–54

By essentially the same procedure set forth in Preparative Example 46, only substituting the compounds in Table 7, column 2, the compounds in column 3 were prepared (CMPD).

TABLE 7
| Prep. Ex. | Column 2 | Column 3 | CMPD |
|---|---|---|---|
| 47 | 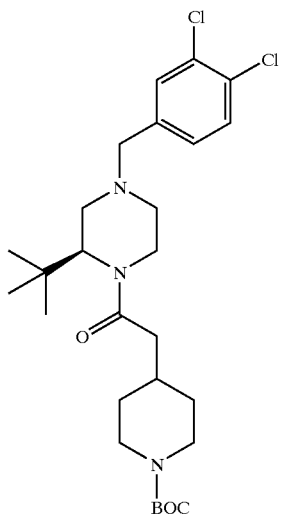 | 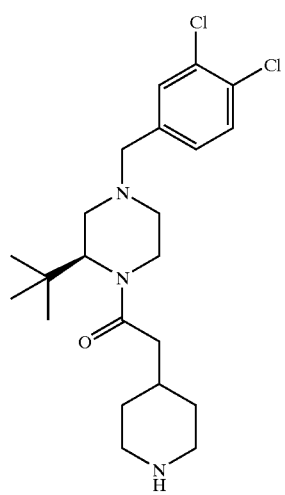 | — |
| 48 | 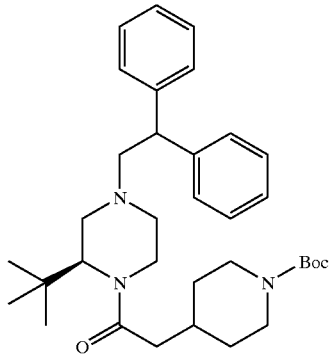 | 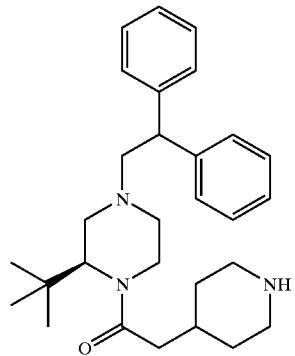 | — |
| 49 | 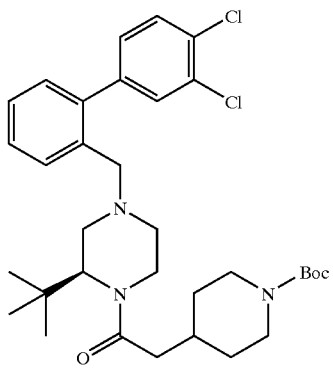 | 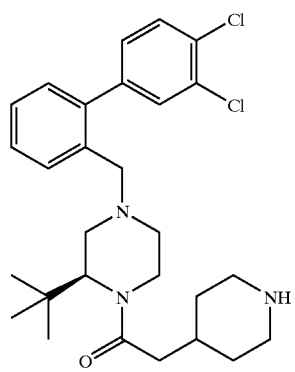 | LCMS: MH$^+$ = 502 |

TABLE 7-continued

| Prep. Ex. | Column 2 | Column 3 | CMPD |
|---|---|---|---|
| 50 | | | LCMS: MH$^+$ = 503 |
| 51 | | | — |
| 52 | | | LCMS: MH$^+$ = 480 |

TABLE 7-continued

| Prep. Ex. | Column 2 | Column 3 | CMPD |
|---|---|---|---|
| 53 | | | LCMS: MH$^+$ = 480 |
| 54 | | | — |

Preparative Example 55

Step A:

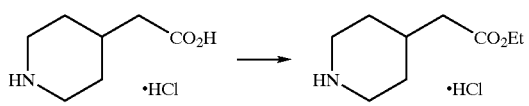

To a solution of piperidine-4-acetic acid (10.0 g, 70.0 mmol) in EtOH (100 mL) was added concentrated HCl (2.68 mL, 2.2 eq.). The resulting solution was heated at reflux for 12 hours. The reaction mixture was concentrated under reduced pressure and used without further purification (10 g, 84% yield).

Step B:

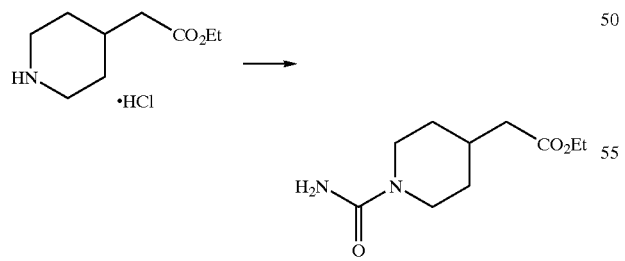

To a solution of the product from Step A above, (2.0 g, 9.6 mmol) in CH$_2$Cl$_2$ (30 mL) at 0° C. was added TMSNCO (6.3 mL, 5.0 eq.) followed by TEA (2.0 mL, 1.5 eq.). The resulting solution was stirred at 0° C. for 3 hours, quenched with water and diluted with saturated NaHCO$_3$. The mixture was extracted with CH$_2$Cl$_2$. The combined organics were dried over Na$_2$SO$_4$, filtered, and concentrated. The crude product was purified by flash chromatography using an 8% (10% NH$_4$OH in MeOH) in CH$_2$Cl$_2$ as eluent (1.2 g, 60% yield) FABMS: MH$^+$=215.

Step C:

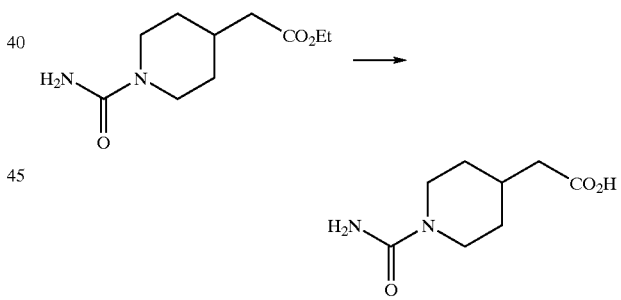

A solution of the product from Step B above, (1.23 g, 5.7 mmol) and LiOH (0.33 g, 2.4 eq.) in CH$_2$Cl$_2$ (29 mL), EtOH (29 mL) and water (14 mL) was heated at reflux for 3 hours. The resulting solution was cooled to room temperature, neutralized by the addition of 1N HCl (16.1 mL, 2.98 eq.) and concentrated under reduced pressure. The reaction product was further dried by the azeotropic removal of water with toluene to yield a gum (1.1 g, quantitative yield). FABMS: MH$^+$=187.

EXAMPLES

Examples 100–102

By essentially the same procedure set forth in Preparative Example 41 only using the chlorides in column 2 of Table 6, and the piperazines in Column 3, the products in Column 4, were prepared.

TABLE 6
| Ex. | Column 2 | Column 3 | Column 4 | CMPD |
|---|---|---|---|---|
| 100 | 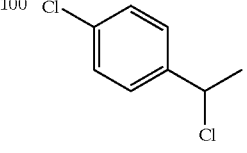 | 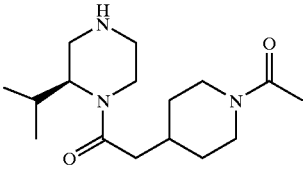 | 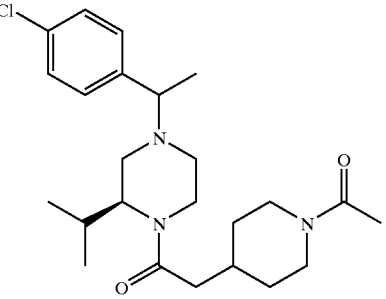 | LCMS: MH+ = 434. |
| 101 | 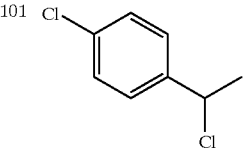 | 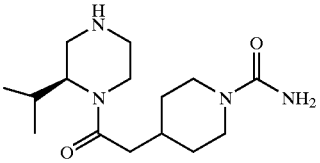 | 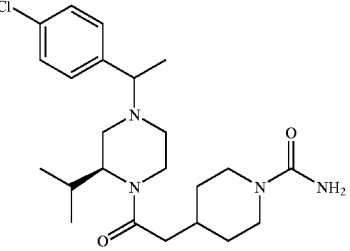 | LCMS: MH+ = 435 mp = 76–82° C. |
| 102 | 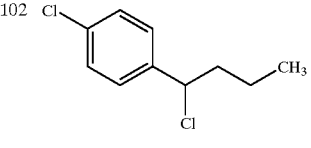 | 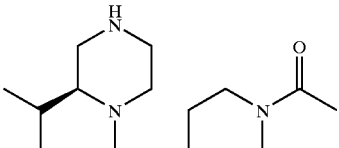 | 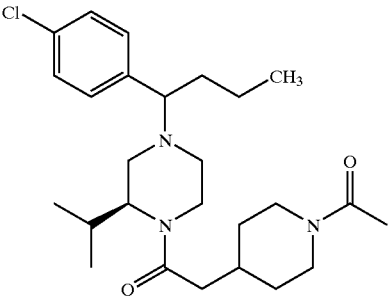 | LCMS: MH+ = 462. |
Example 103
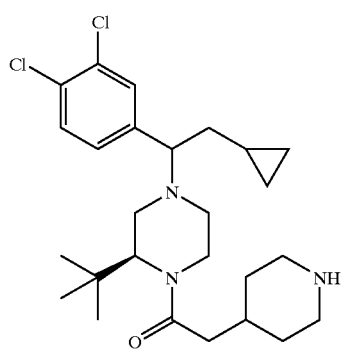
→
-continued
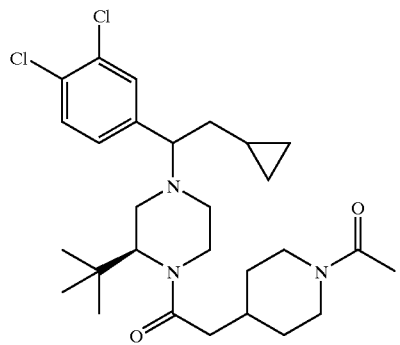

To a solution of the product from Preparative Example 46 (0.027 g, 0.056 mmol) in $CH_2Cl_2$ (5 mL) at 0° C. was added TEA (0.039 mL, 5 eq.) and AcCl (0.006 mL, 1.2 eq.). The reaction mixture was warmed to room temperature and stirred until TLC showed consumption of starting material (20 minutes). The reaction was quenched by the addition of saturated $NaHCO_3$ and extracted with $CH_2Cl_2$. The combined organics were dried over $Na_2SO_4$, filtered and concentrated. The crude product was purified by flash chromatography using a 5% (10% $NH_4OH$ in MeOH) in $CH_2Cl_2$ solution as eluent to yield a solid mp=60–69° C. LCMS: $MH^+$=522.

Examples 104–111

By essentially the same procedure set forth in Example 103 only substituting the products from Preparative Examples 47–54 shown in Table 8, column 2, the compounds shown in column 3 were prepared:

TABLE 8

| Ex. | Column 2 | Column 3 | Phys. data |
|---|---|---|---|
| 104 | | | LCMS: $MH^+$ = 468; mp = 49–53° C. |
| 105 | | | LCMS: $MH^+$ = 490. |
| 106 | | | LCMS: $MH^+$ = 544; mp = 62.1–63.6° C. |

TABLE 8-continued
| Ex. | Column 2 | Column 3 | Phys. data |
|---|---|---|---|
| 107 | 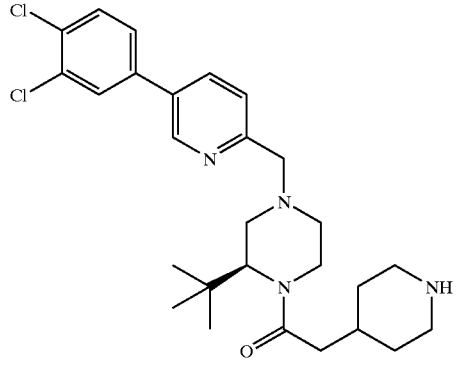 | 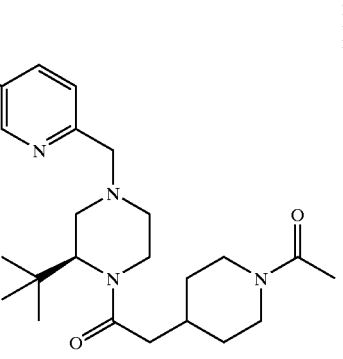 | LCMS: MH+ = 545; mp = 145.7–147.0° C. |
| 108 | 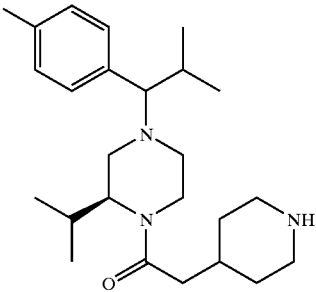 | 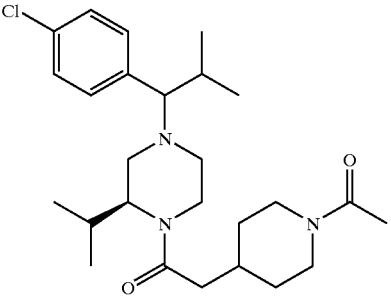 | LCMS: MH+ = 462. |
| 109 | 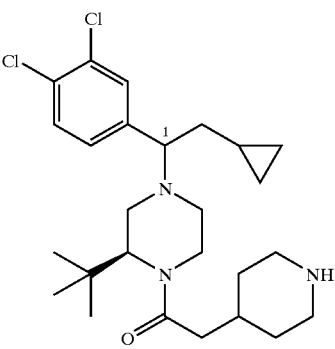 | 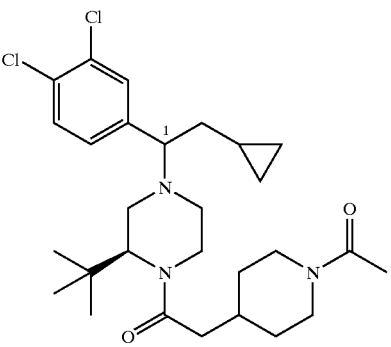 | LCMS: MH+ = 522; mp = 61–63° C. |

TABLE 8-continued

| Ex. | Column 2 | Column 3 | Phys. data |
|---|---|---|---|
| 110 | | | LCMS: MH+ = 522; mp = 61–65° C. |
| 111 | | | LCMS: MH+ = 564; mp = 61–63° C. |

Example 112

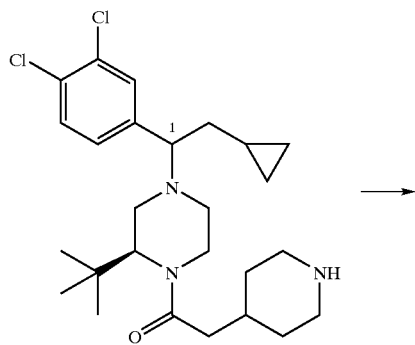

→

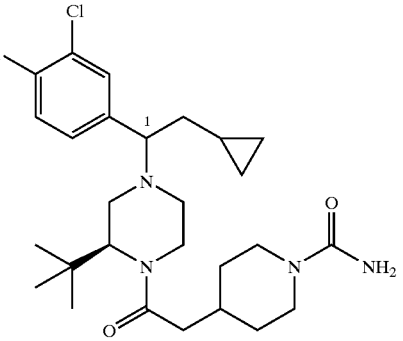

To a solution of the product from Preparative Example 52 (0.06 g, 0.125 mmol) in CH$_2$Cl$_2$ (3 mL) at 0° C. was added TEA (0.087 mL, 5 eq.) and TMSNCO (0.084 mL, 5 eq.). The reaction mixture was stirred until TLC showed consumption of starting material (30 minutes). The reaction was quenched by the addition of saturated NaHCO$_3$ and extracted with CH$_2$Cl$_2$. The combined organics were dried over Na$_2$SO$_4$, filtered and concentrated. The crude product was purified by flash chromatography using a 5% (10% NH$_4$OH in MeOH) in CH$_2$Cl$_2$ solution as eluent to yield a solid; LCMS: MH+=523; mp=95–98° C.

Examples 113–117

By essentially the same procedure set forth in Example 112 only substituting the products from Preparative Examples 47, 49–50 and 53–54 shown in Table 9, column 2, the compounds shown in column 3 (CMPD) were prepared:

TABLE 9
| Ex. | Column 2 | Column 3 | CMPD |
|---|---|---|---|
| 113 | 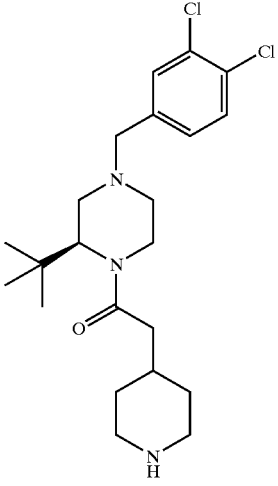 | | LCMS: MH+ = 469; mp = 80–85° C. |
| 114 | 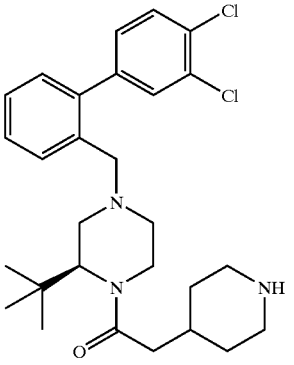 | | LCMS: MH+ = 545; mp = 98.8–102.4° C. |
| 115 | 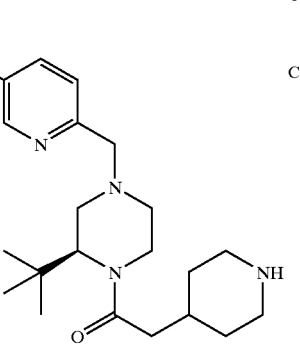 | | LCMS: MH+ = 546; mp = 95.2–98.0° C. |

TABLE 9-continued

| Ex. | Column 2 | Column 3 | CMPD |
|---|---|---|---|
| 116 | | | LCMS: MH+ = 523; mp = 91–94° C. |
| 117 | | | LCMS: MH+ = 565; mp = 76–80° C. |

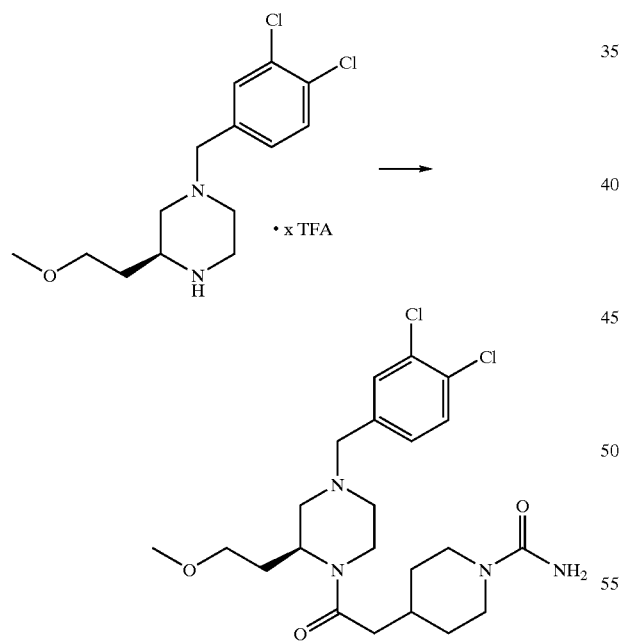

Example 118

A solution of the product from Preparative Example 33 (0.64 mmol), carboxamidopiperadineacetic acid (0.29 g, 1.3 eq.), DEC (0.17 g, 1.3 eq.), HOBt (0.12 g, 1.3 eq.), and NMM (0.36 mL, 5.0 eq.) in DMF (8.0 mL) was stirred at room temperature 5 days. The reaction was quenched by the addition of 1N NaOH and extracted with $CH_2Cl_2$. The combined organics were dried over $Na_2SO_4$, filtered, and concentrated. The crude product was purified by flash chromatography using a 15% MeOH in $CH_2Cl_2$ solution as eluent (0.13 g, 42% yield); FABMS: MH+=471; mp=63–68° C.

What is claimed is:

1. A compound of the formula (I):

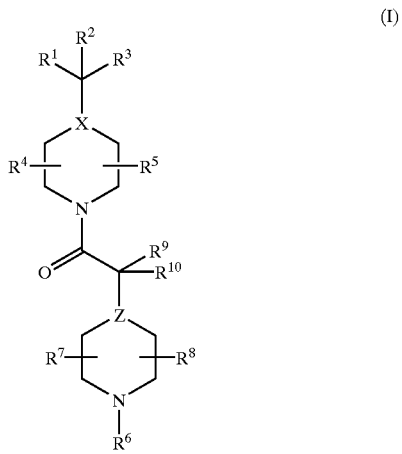

or a pharmaceutically acceptable salt of the compound wherein, $R^1$ is selected from the group consisting of aryl, heteroaryl, arylalkyl, heteroarylalkyl and diphenylalkyl, each optionally substituted with one to six groups selected from the group consisting of:
a) halogen;
b) —$OCF_3$ or —$OCHF_2$;
c) —$CF_3$;
d) —CN;
e) alkyl or $R^{18}$-alkyl;

f) heteroalkyl or $R^{18}$-heteroalkyl;
g) aryl or $R^{18}$-aryl;
h) heteroaryl or $R^{18}$-heteroaryl;
i) arylalkyl or $R^{18}$-arylalkyl;
j) heteroarylalkyl or $R^{18}$-heteroarylalkyl;
k) hydroxy;
l) alkoxy;
m) aryloxy;
n) —$SO_2$-alkyl;
o) —$NR^{11}R^{12}$;
p) —$N(R^{11})C(O)R^{13}$,
q) methylenedioxy;
r) difluoromethylenedioxy;
s) trifluoroalkoxy;
t) —$SCH_3$ or —$SCF_3$; and
u) —$SO_2CF_3$ or —$NHSO_2CF_3$;

$R^2$ and $R^3$ are each independently selected from the group consisting of H, —OH, alkoxy, alkyl, cycloalkyl, heterocycloalkyl, cycloalkylalkyl, trifluoroalkyl, heteroalkyl, arylalkyl, heteroarylalkyl, arylalkoxy, heteroarylalkoxy, —$(CH_2)_n$—$NR^{11}R^{12}$ and —$(CH_2)_n$—$SR^{11}$, provided that when X is N, then $R^2$ and $R^3$ are each not —OH, alkoxy, arylalkoxy or heteroarylalkoxy;

$R^4$, $R^5$, $R^7$ and $R^8$ are each independently selected from the group consisting of H, —$OR^{14}$, —$NR^{11}R^{12}$, —$N(R^{11})C(O)R^{13}$, alkyl, aryl, cycloalkyl, arylalkyl, heteroalkyl, heteroaryl, heteroarylalkyl, heterocycloalkyl,

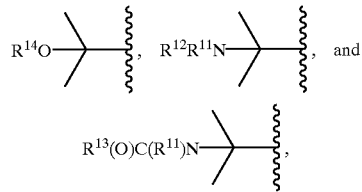

provided that when Z and/or X is N, then $R^4$, $R^5$, $R^7$ and $R^8$ are each not —$OR^{14}$, —$NR^{11}R^{12}$ or —$N(R^{11})C(O)R^{13}$;

$R^6$ is selected from the group consisting of —$C(O)R^{15}$ and —$SO_2R^{15}$;

$R^9$ and $R^{10}$ are each independently selected from the group consisting of H, F, —$CF_3$, —$CHF_2$, alkyl, cycloalkyl, arylalkyl, heteroalkyl, heteroarylalkyl, heterocyoloalkyl, hydroxy, alkoxy, aryloxy, —$NR^{11}R^{12}$ and —$N(R^{11})C(O)R^{13}$, provided that when Z is N, then $R^9$ and $R^{10}$ are each not F, hydroxy, alkoxy, aryloxy, —$NR^{11}R^{12}$ or —$N(R^{11})C(O)R^{13}$;

$R^{11}$ is selected from the group consisting of H, alkyl, aryl and heteroaryl;

$R^{12}$ is selected from the group consisting of H, alkyl, aryl and heteroaryl;

$R^{13}$ is selected from the group consisting of alkyl, alkoxy and aryloxy;

$R^{14}$ is selected from the group consisting of H, alkyl, aryl and heteroaryl;

$R^{15}$ is selected from the group consisting of —$NR^{16}R^{17}$, —$OR^{16}$, alkyl, cycloalkyl, heterocycloalkyl, aryl, arylalkyl and heteroarylalkyl, each optionally substituted with $R^{18}$;

$R^{16}$ and $R^{17}$ are each independently selected from the group consisting of alkyl, aryl, arylalkyl, heteroalkyl and heteroaryl, each optionally substituted with $R^{18}$, and H, provided that when $R^{15}$ is —$OR^{16}$, $R^{16}$ is not H;

$R^{18}$ is one to four substituents each independently selected from the group consisting of lower alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl;

X is N;

Z is C;

and n is 1–4, wherein the term "heteroaryl" refers to 5- or 10-membered single or benzofused aromatic ring consisting of 1 to 3 heteroatoms independently selected from the group consisting of —O—, —S, and —N=, provided that the rings do not possess adjacent oxygen and/or sulfur atoms, wherein said heteroaryl can be unsubstituted or substituted with one, two, or three substituents independently selected from lower alkyl, halo, cyano, nitro, haloalkyl, hydroxy, alkoxy, carboxy, carboxyalkyl, carboxamide, mercapto, amino, alkylamino and dialkylamino; the term "heteroarylalkyl" refers to a heteroaryl group bonded through an alkyl group; the term "heterocyoloalkyl" refers to a non-aromatic, heterocyclic ring of 3–7 atoms containing 1–3 heteroatoms selected from N, O and S; and the term "heterocycloalkylalkyl" refers to a heterocycloalkyl group bonded through an alkyl group.

2. The compound of claim 1 wherein, $R^1$ is selected from the group consisting of aryl and heteroaryl, each optionally substituted with one to six groups selected from the group consisting of:

a) halogen;
b) —$OCF_3$;
c) —$CF_3$;
d) —CN;
e) (C1–C20)alkyl or $R^{18}$—(C1–C20)alkyl;
f) heteroalkyl or $R^{18}$-heteroalkyl;
g) aryl or $R^{18}$-aryl;
h) heteroaryl or $R^{18}$-heteroaryl;
i) arylalkyl or $R^{18}$-arylalkyl;
j) heteroarylalkyl or $R^{18}$-heteroarylalkyl;
k) hydroxy;
l) alkoxy;
m) aryloxy;
n) —$SO_2$-alkyl;
o) —$NR^{11}R^{12}$;
p) —$N(R^{11})C(O)R^{13}$;
q) methylenedioxy;
r) difluoromethylenedioxy;
s) trifluoroalkoxy;
t) —$SCH_3$; and
u) —$SO_2CF_3$;

$R^4$, $R^5$, $R^7$ and $R^8$ are each independently selected from the group consisting of H, alkyl, heteroalkyl, aryl, cycloalkyl, arylalkyl, heteroaryl, heteroarylalkyl, heterocycloalkyl, —$OR^{14}$, —$NR^{11}R^{12}$,

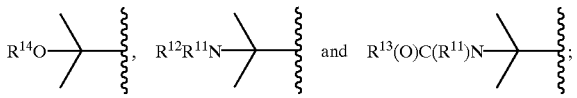

$R^{11}$ is selected from the group consisting of H alkyl;

Z is C; and n is 1–3.

3. The compound of claim 1, wherein:

$R^1$ is selected from the group consisting of aryl and heteroaryl, each optionally substituted with one to six groups selected from the group consisting of:

a) halogen;
b) —$OCF_3$;
c) —$CF_3$;
e) (C1–C6)alkyl or $R^{18}$—(C1–C6)alkyl;
f) heteroalkyl or $R^{18}$-heteroalkyl;
g) aryl or $R^{18}$-aryl;
i) arylalkyl or $R^{18}$-arylalkyl;
j) heteroarylalkyl or $R^{18}$-heteroarylalkyl; and
l) alkoxy; and
s) trifluoroalkoxy;

$R^4$, $R^5$, $R^7$ and $R^8$ are each independently selected from the group consisting of H, —$OR^{14}$, —$NR^{11}R^{12}$, alkyl, aryl, cycloalkyl, arylalkyl, heteroalkyl, heteroarylalkyl, heterocycloalkyl,

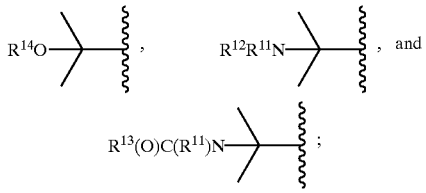

$R^{11}$ is selected from the group consisting of H and alkyl;

Z is C; and n is 1–3.

4. The compound of claim 1 wherein:

$R^1$ is selected from the group consisting of aryl and heteroaryl, each optionally substituted with one to six groups selected from the group consisting of:

a) halogen;
b) —$OCF_3$;
c) —$CF_3$;
e) (C1–C6)alkyl or $R^{18}$—(C1–C6)alkyl;
l) alkoxy; and
s) trifluoroalkoxy;

$R^2$ and $R^3$ are each independently selected from the group consisting of H, alkyl, and heteroalkyl;

$R^4$, $R^5$, $R^7$ and $R^8$ are each independently selected from the group consisting of H, alkyl, heteroalkyl, aryl, cycloalkyl, arylalkyl, heteroaryl, heteroarylalkyl, heterocycloalkyl, —$OR^{14}$, —$NR^{11}R^{12}$, $R^{14}O$—, $R^{12}R^{11}N$—, and $R^{13}(O)C(R^{11})N$—;

$R^{11}$ is selected from the group consisting of H and alkyl; and

Z is C.

5. The compound of claim 1 wherein, $R^1$ is selected from the group consisting of aryl and heteroaryl, each optionally substituted with one to six groups selected from the group consisting of:

a) halogen;
b) —$OCF_3$;
c) —$CF_3$;
l) alkoxy; and
s) trifluoroalkoxy;

$R^2$ is alkyl;

$R^3$ is H;

$R^4$ and $R^5$ are each independently selected from the group consisting of H, (C1–C6)alkyl, heteroalkyl and

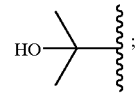

$R^7$ is selected from the group consisting of H, alkyl, —$OR^{14}$ and —$NR^{11}R^{12}$;

$R^8$ is selected from the group consisting of H, alkyl, aryl and heteroaryl;

$R^{11}$ is selected from the group consisting of H and alkyl; and

Z is C.

6. The compound of claim 1 wherein, $R^1$ is selected from the group consisting of phenyl and pyridyl, each optionally substituted with one to six groups selected from the group consisting of:

a) Br; F or Cl;
b) —$OCF_3$;
c) —$CF_3$;
l) methoxy, ethoxy or cyclopropylmethoxy; and
s) —$OCH_2CF_3$;

$R^2$ is selected from the group consisting of methyl, ethyl, propyl, cyclopropylmethyl and t-butyl;

$R^3$ is H;

$R^4$ and $R^5$ are each independently selected from the group consisting of H, methyl, ethyl, isopropyl and t-butyl;

$R^7$ is selected from the group consisting of H, —$OR^{14}$ and alkyl;

$R^8$, $R^9$, $R^{10}$, $R^{11}$, $R^{12}$ and $R^{14}$ are each independently selected from the group consisting of H and alkyl;

$R^{13}$ is alkyl;

$R^{15}$ is selected from the group consisting of —$NR^{16}R^{17}$, —$OR^{18}$ and alkyl;

$R^{16}$ and $R^{17}$ are each independently selected from the group consisting of H and alkyl; and Z is C.

7. The compound of claim 1, or the pharmaceutically acceptable salt of the compound selected from the group consisting of:
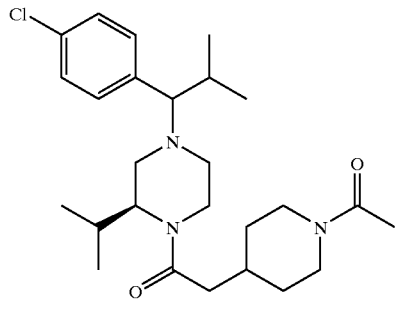
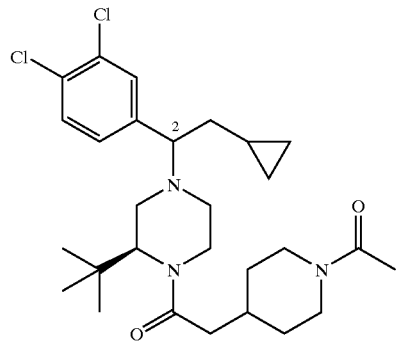
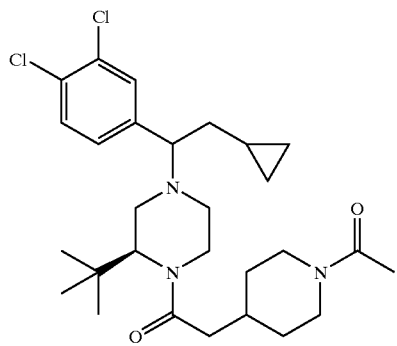
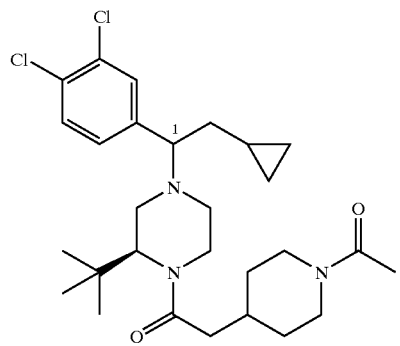
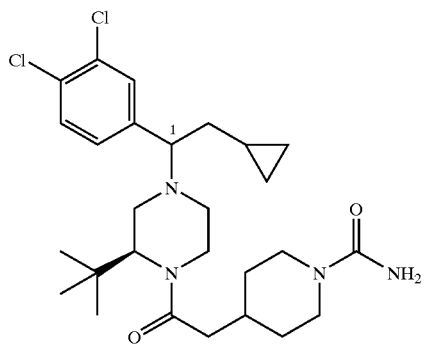
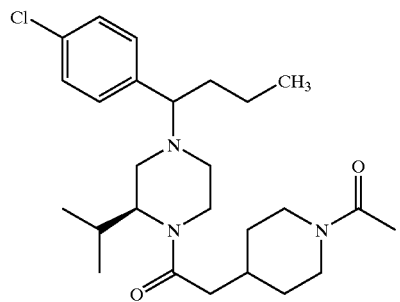
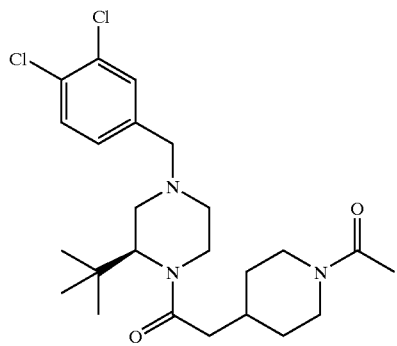
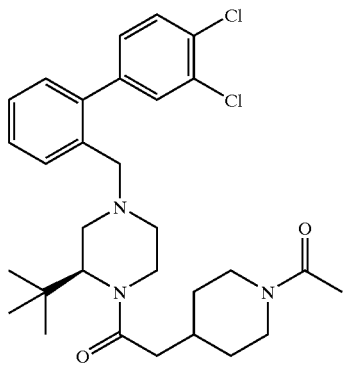

-continued
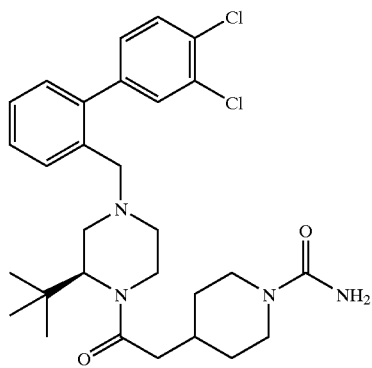
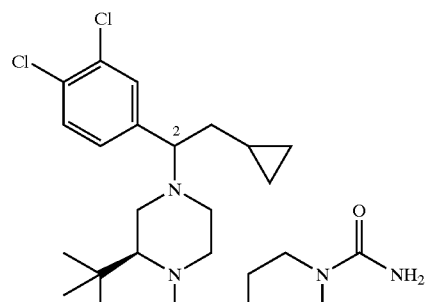
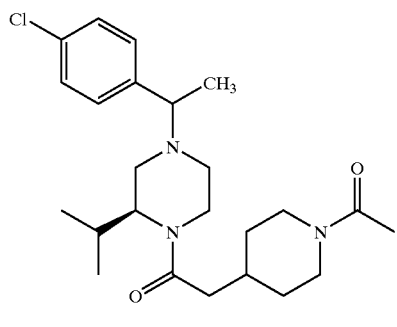
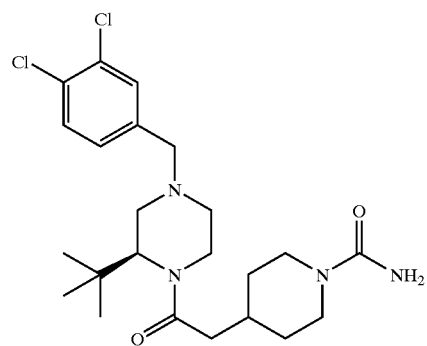
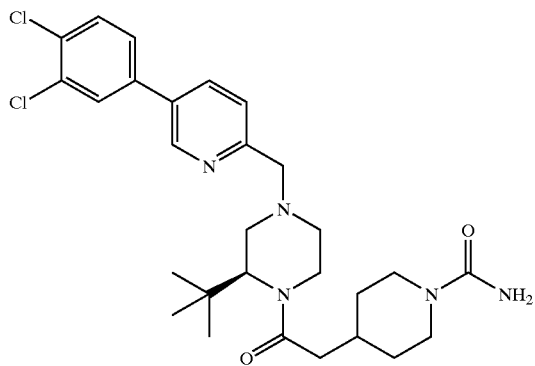
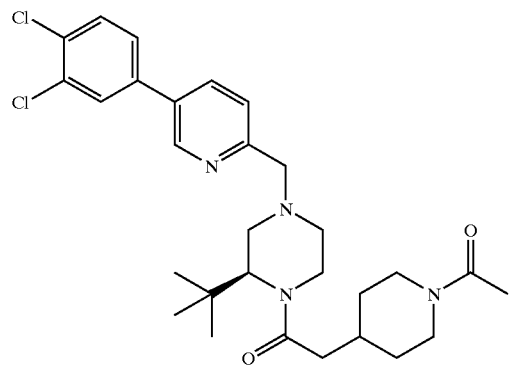
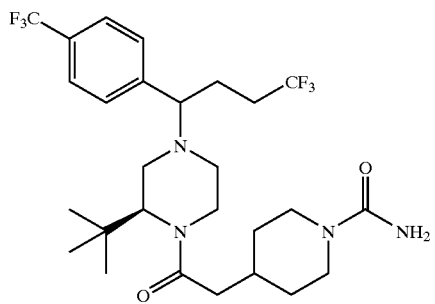
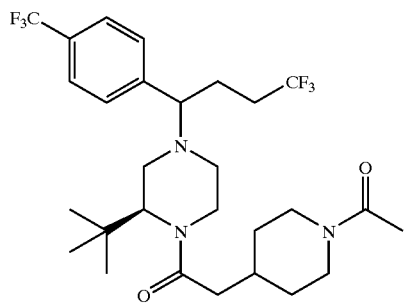

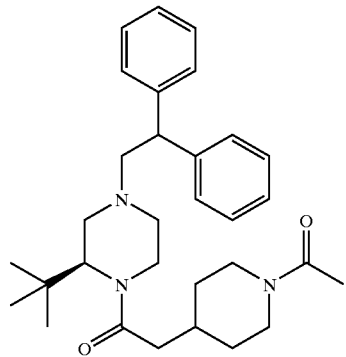
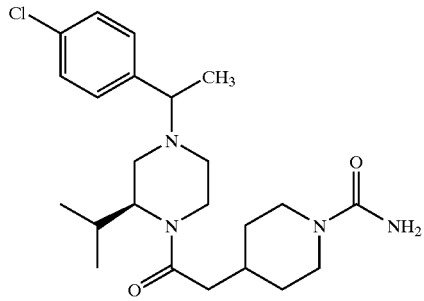
and
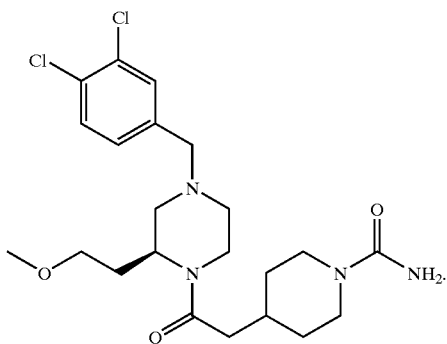
8. The compound according to claim 1, or the pharmaceutically acceptable salt of the compound selected from the group consisting of:
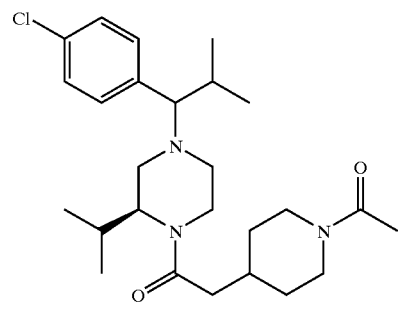
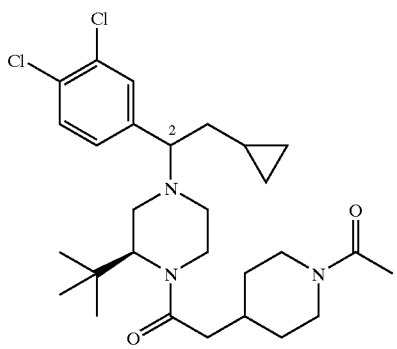

-continued

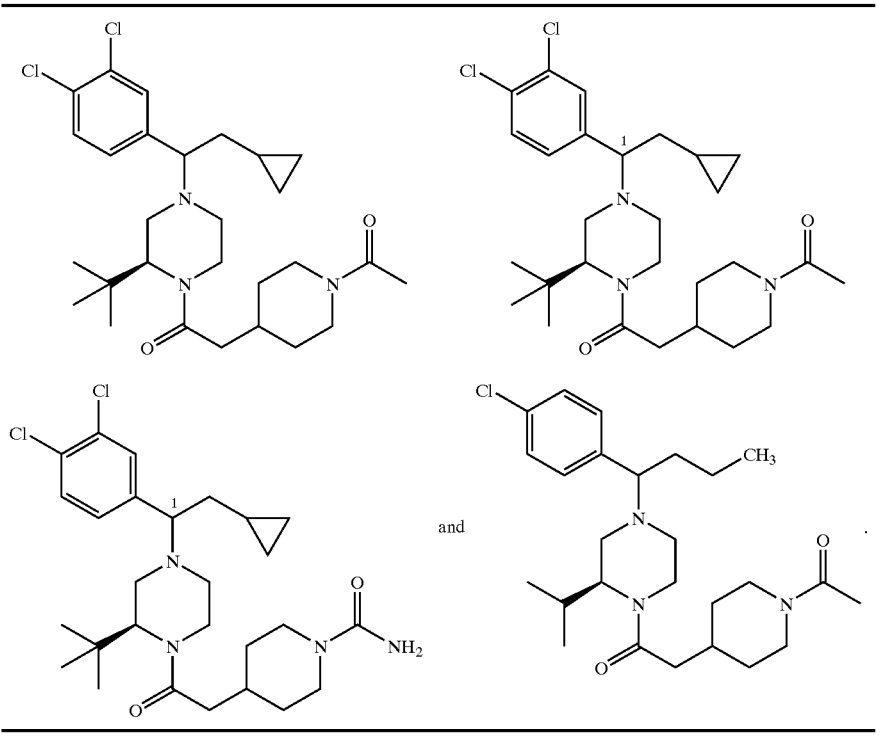

9. The compound according to claim 8, or the pharmaceutically acceptable salt of the compound which is:

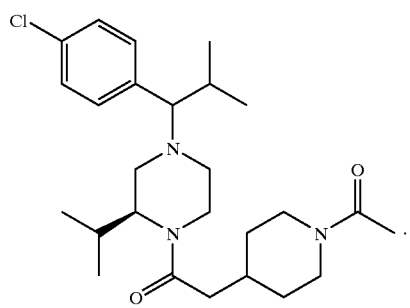

10. The compound according to claim 8, or the pharmaceutically acceptable salt of the compound which is:

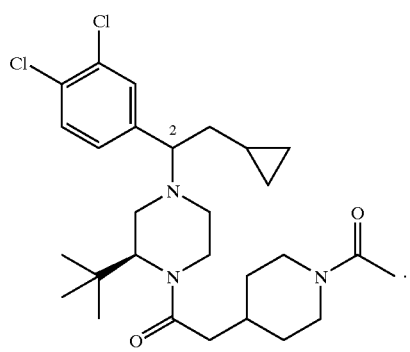

11. The compound according to claim 8, or the pharmaceutically acceptable salt of the compound which is:

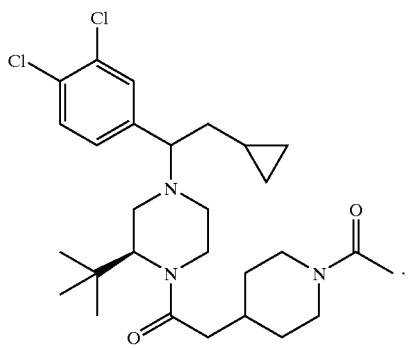

12. The compound according to claim 8, or the pharmaceutically acceptable salt of the compound which is:

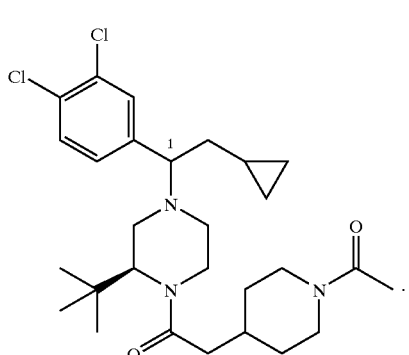

13. The compound according to claim 8, or the pharmaceutically acceptable salt of the compound which is:

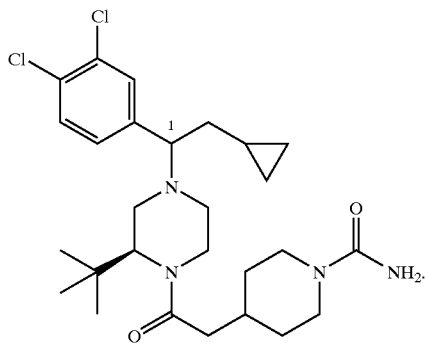

14. The compound according to claim 8, or the pharmaceutically acceptable salt of the compound which is:

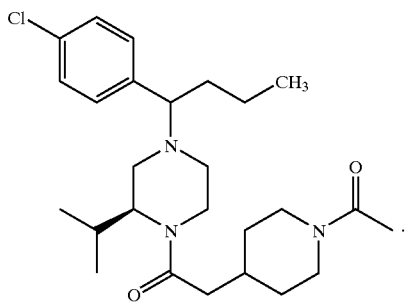

15. A pharmaceutical composition comprising the compound of claim 1, and a pharmaceutically acceptable carrier therefor.

16. A method of inhibiting Type 3 17β-hydroxysteroid dehydrogenases and thereby treating an androgen dependent disease wherein the androgen dependent disease is selected from the group consisting of prostate cancer, benign prostatic hyperplasia, prostatic intraepithelial neoplasia, hirsutism, acne, androgenic alopecia, and polycystic ovary syndrome which method comprises administering to patient a therapeutically effective amount of the compound of claim 1, or the pharmaceutically acceptable salt thereof.

17. The method of claim 16, wherein the androgen dependent disease is selected from the group consisting of prostate cancer, benign prostatic hyperplasia and prostatic intraepithelial neoplasia.

18. A method of inhibiting Type 3 17β-hydroxysteroid dehydrogenases, which comprises administering to a patient a therapeutically effective amount of the compound of claim 1, or the pharmaceutically acceptable salt thereof.

* * * * *

UNITED STATES PATENT AND TRADEMARK OFFICE
CERTIFICATE OF CORRECTION

PATENT NO. : 6,969,718 B2
DATED : November 29, 2005
INVENTOR(S) : Timothy J. Guzi et al.

It is certified that error appears in the above-identified patent and that said Letters Patent is hereby corrected as shown below:

Column 70,
Line 28, correct "heterocyoloalkyl" to -- heterocycloalkyl --.

Column 71,
Line 8, correct "H alkyl;" to -- H and alkyl --.

Column 72,
Line 46, correct "Br." to -- Br, --.
Line 64, correct "-OR18" to -- -OR16 --.

Column 82,
Line 9, correct "treating an androgen" to -- treating or preventing an androgen --.

Signed and Sealed this

Seventh Day of February, 2006

JON W. DUDAS
*Director of the United States Patent and Trademark Office*